US010603345B2

(12) United States Patent
Luo et al.

(10) Patent No.: US 10,603,345 B2
(45) Date of Patent: Mar. 31, 2020

(54) PHARMACEUTICAL COMPOSITION FOR TREATING RESPIRATORY DISEASE

(71) Applicants: Kunming Institute of Botany, The Chinese Academy of Sciences, Kunming (CN); Kunming Beiao Technology Company Limited, Kunming (CN)

(72) Inventors: Xiaodong Luo, Kunming (CN); Yunli Zhao, Kunming (CN); Jianhua Shang, Kunming (CN); Yaping Liu, Kunming (CN); Yifen Wang, Kunming (CN)

(73) Assignees: Kunming Institute of Botany, The Chinese Academy of Sciences, Kunming (CN); Kunming Beiao Technology Company Limited, Kunming (CN)

( * ) Notice: Subject to any disclaimer, the term of this patent is extended or adjusted under 35 U.S.C. 154(b) by 56 days.

(21) Appl. No.: 15/775,372

(22) PCT Filed: Nov. 10, 2016

(86) PCT No.: PCT/CN2016/105318
§ 371 (c)(1),
(2) Date: May 10, 2018

(87) PCT Pub. No.: WO2017/080485
PCT Pub. Date: May 18, 2017

(65) Prior Publication Data
US 2018/0344792 A1 Dec. 6, 2018

(30) Foreign Application Priority Data

Nov. 11, 2015 (CN) .......................... 2015 1 0770997

(51) Int. Cl.
*A61K 36/24* (2006.01)
*A61K 31/439* (2006.01)
(Continued)

(52) U.S. Cl.
CPC ............ *A61K 36/24* (2013.01); *A61K 31/395* (2013.01); *A61K 31/405* (2013.01);
(Continued)

(58) Field of Classification Search
CPC ...................................................... A61K 36/24
See application file for complete search history.

(56) References Cited

FOREIGN PATENT DOCUMENTS

| CN | 101 084 951 A | 12/2007 |
| CN | 100 563 670 C | 12/2009 |
| CN | 103655651 A | 3/2014 |
| CN | 105456263 A | 4/2016 |

OTHER PUBLICATIONS

Google Patents translaltion of Kunming Plant Research Institute of the China Academy of Sciences, CN 101084951 B, 2011.*
(Continued)

*Primary Examiner* — Rosanne Kosson
(74) *Attorney, Agent, or Firm* — Christensen O'Connor Johnson Kindness PLLC

(57) ABSTRACT

The invention provides a pharmaceutical composition for treating a respiratory disease, wherein the pharmaceutical composition comprises one or more components selected from picrinine, vallesamine, scholaricine, and 19-epischolaricine. The pharmaceutical composition has a good protective effect on the respiratory system, and can be used in treatment of a relevant disease.

15 Claims, 1 Drawing Sheet

(51) Int. Cl.
 A61K 31/395 (2006.01)
 A61K 31/405 (2006.01)
 A61P 11/06 (2006.01)
 A61P 29/00 (2006.01)
(52) U.S. Cl.
 CPC ............ *A61K 31/439* (2013.01); *A61P 11/06* (2018.01); *A61P 29/00* (2018.01); *A61K 2236/33* (2013.01)

(56) References Cited

OTHER PUBLICATIONS

Shang, J.-H., et al., "Pharmacological Evaluation of Alstonia Scholaris: Anti-inflammatory and Analgesic Effects," Journal of Ethnopharmacology, 129:174-181, 2010.

Shang, J.-H., et al., "Pharmacological Evaluation of Alstonia Scholaris: Anti-tussive, Anti-asthmatic and Expectorant Activities," Journal of Ethnopharmacology, 129:293-298, 2010.

Partial Supplementary European Search Report dated Jun. 11, 2019, issued in corresponding International Application No. PCT/CN2016/105318, filed Nov. 10, 2016, 16 pages.

Cao, J. et al. "Characterization of Chemical Constituents and Rats Metabolites of an Alkaloidal Extract of Alstonia scholaris Leaves by Liquid Chromatography Coupled With Mass Spectrometry," Journal of Chromatography B, 1026:43-55, 2016.

Cao, J., et al., "Characterization of Chemical Constituents and Rats Metabolites of an Alkaloidal Extract of Alstonia Scholaris Leaves by Liquid Chromatography Couple with Mass Spectrometry," Journal of Chromatography B, pp. 43-55, 2016.

Cai, X-H., et al., "Novel Alkaloids from Alstonia Scholaris," Z. Nautrforsch 2010, pp. 1164-1168.

European Search Report dated Oct. 8, 2019, issued in corresponding European International No. 16 86 3661, filed Nov. 10, 2016, 15 pages.

* cited by examiner

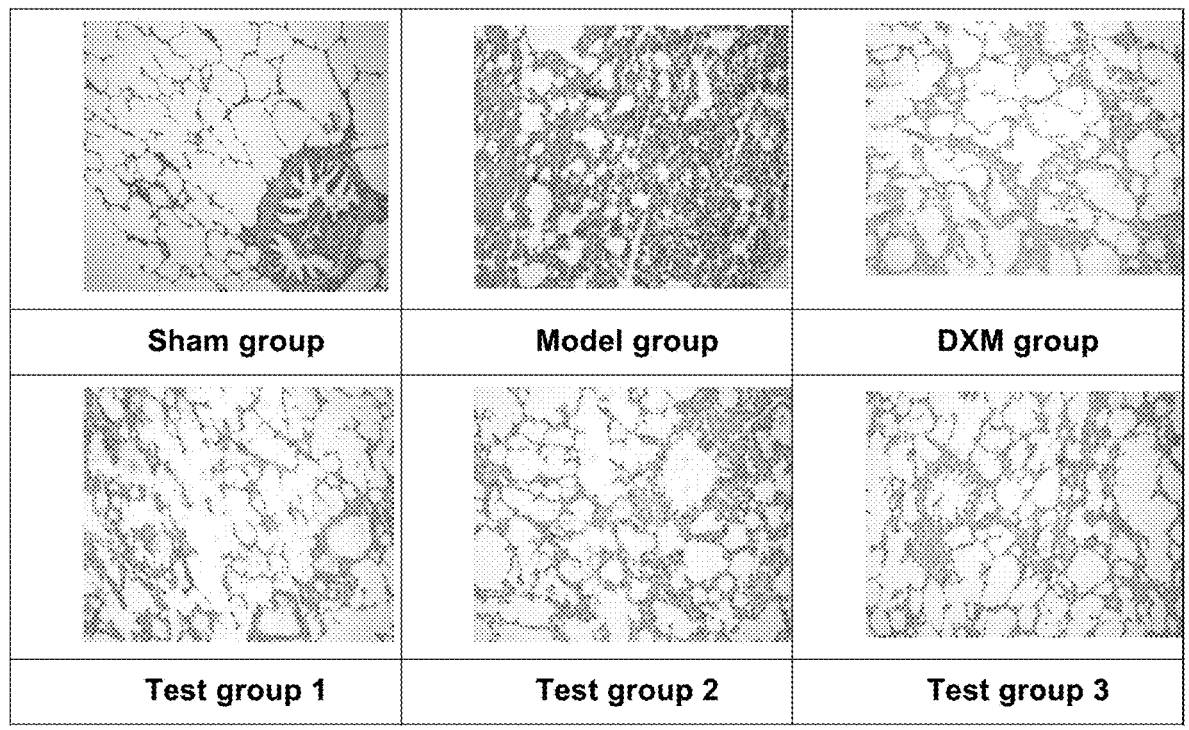

PHARMACEUTICAL COMPOSITION FOR TREATING RESPIRATORY DISEASE

TECHNICAL FIELD

The invention relates to the field of medical technology, particularly relates to a pharmaceutical composition, and use thereof in the manufacture of a medicament for treating a respiratory disease.

BACKGROUND ART

Respiratory disease is a common and frequently-occurring disease, which has the main pathologic changes in trachea, bronchi, lung and pleural cavity. Mild patients generally have cough, chest pain, and have breathing disturbed, while severe patients have difficulty in breathing, have hypoxia, or even die due to respiratory failure.

Since the 21$^{st}$ century, with the rapid development of economics and constantly accelerating process of urbanization in China, air pollution has become an inevitable practical issue. The respiratory problems caused thereby have drawn global attention. According to a large number of epidemiological surveys and statistics, respiratory disease (not including lung cancer) accounted for 13.1% of death in urban residents (ranking fourth among various causes of death) and 16.4% in rural residents (ranking third among various causes of death).

Airway inflammatory disease, which is one of the common and frequently-occurring respiratory diseases in clinic, refers to inflammatory disease in upper airway (mainly including nose, pharynx and larynx) and lower airway (mainly including trachea). It is characterized by airway inflammation and tissue remodeling, and is manifested as changes in epithelial cells, mucosal and submucosal exudation and infiltration of inflammatory cell, hypertrophy and hyperplasia of goblet cells, strong glandular secretion, sub-epithelial edema, basement membrane thickening and fibrosis, etc. Its pathogenic cause is mainly associated with smoking, air pollution, infection, harmful gas, dust inhalation, and intrinsic factor of organism, etc. For site of the organism in direct contact with inhalation irritants, symbionts, and pathogens, airway barrier protection is weakened, which stimulates the participation of active oxygen system, various inflammatory cell and inflammatory mediators, thereby aggravating the inflammatory response. Therefore, the treatment against inflammation has become the most critical part in the treatment of airway inflammatory disease.

Chronic obstructive pulmonary disease (COPD) is a chronic, refractory, senile respiratory disease, characterized by incompletely reversible airflow limitation, and has a high disability rate and mortality. Many inflammatory cells such as neutrophils, alveolar macrophages and lymphocytes promote the occurrence and development of chronic airway inflammation in different phases by releasing various bioactive substances such as interleukin, tumor necrosis factor and so on. Airway mucus hypersecretion and inflammatory response, considered as one of the important causes for COPD, eventually lead to airway obstruction and airflow limitation.

Bronchial asthma is a common respiratory disease in adults and children, and its pathological characteristic is chronic airway inflammation in which various inflammatory cells are involved, such as eosinophils, lymphocytes, mast cells and neutrophils.

Pulmonary fibrosis, particularly idiopathic pulmonary fibrosis, has been considered for a long time as a progressive and substantially irreversible pathological change. That is, it starts from infiltration of inflammatory cell in lower respiratory tract, gradually leads to injury to alveolar epithelial cells and vascular endothelial cells, is accompanied by the release of cytokines and the like which can promote proliferation of myofibroblasts and alveolar type II epithelial cells, results in extracellular matrix protein and collagen deposition, and finally causes damage to lung structure.

Therefore, how to effectively treat respiratory disease has become a problem to be solved urgently.

There are documents showing that about 80% of drugs available in market are derived from natural products directly or indirectly, and natural drugs have become an important source for the development of therapeutic drugs for human. However, it has not been reported yet that natural drugs have a significant inhibitory effect on respiratory disease.

*Alstoniascholaris* (L.) R. Br., also called *Alstonia scholaris*, is a plant of the genus *Alstonia* of the family Apocynaceae. Its medicinal parts are root, bark and leaf. *Alstonia scholaris* contains various alkaloids having relatively high bioactivities, such as picrinine, vallesamine, scholaricine and 19-epischolaricine.

The structure of picrinine is as follows:

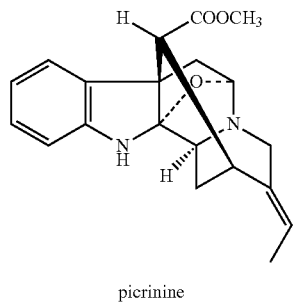 [SMILES: C/C=C1/CN2[C@@H]3C[C@@]45c6ccccc6N[C@]4(O3)[C@@H]2C[C@H]1C5C(=O)OC]

picrinine

The structure of vallesamine is as follows:

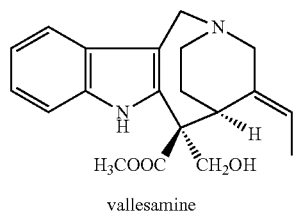

vallesamine

The structure of scholaricine is as follows:

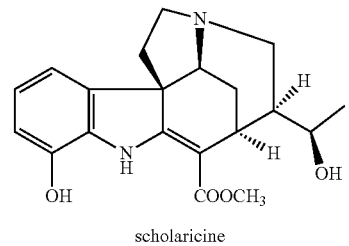 [SMILES: COC(=O)C1=C2Nc3c(O)cccc3[C@@]23CCN2C[C@@H]([C@@H](C)O)[C@@H]1C[C@H]23]

scholaricine

The structure of 19-epischolaricine is as follows:

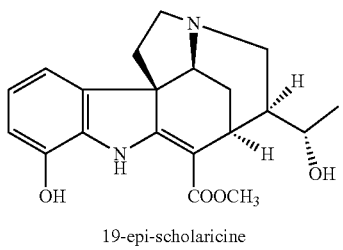 [SMILES: COC(=O)C1=C2Nc3c(O)cccc3[C@@]23CCN2C[C@@H]([C@H](C)O)[C@@H]1C[C@H]23]

19-epi-scholaricine

*Alstonia scholaris* is generally used for the treatment of headache, pneumonia, pertussis, and chronic bronchitis in civilian populations. It has been recorded in the local journal of medicine such as "Lu Chuan Ben Cao", "Selections of Chinese herbal medicines of Yunnan" and "Drug Standards of Yunnan Province" (1974) and "Pharmacopoeia of the People's Republic of China, Vol. 1" (published in 1977). Leaves of *Alstonia scholaris* can clear internal heat, remove phlegm and relieve a cough, and are useful for cough resulted from pulmonary retention of phlegmopyrexia, stethocatharsis, and chronic bronchitis, as well as pertussis having the above-mentioned syndromes. It has not been reported yet that *Alstonia scholaris* has a significant inhibitory effect on respiratory disease.

SUMMARY OF THE INVENTION

Contents of Invention

The inventor of the invention found surprisingly that the alkaloid composition (comprising four main alkaloids, i.e. picrinine, vallesamine, scholaricine and 19-epischolaricine, referred to hereafter as the same) extracted from leaves of *Alstonia scholaris*, or the effective components isolated from the alkaloid composition, i.e. picrinine, vallesamine, scholaricine, and 19-epischolaricine, and any combination thereof, have a significant inhibitory effect on respiratory disease. For example, the alkaloid composition of the invention or the effective components, i.e. picrinine, vallesamine, scholaricine, and 19-epischolaricine, or any combination thereof may decrease the level of IL-8 in lung tissue and serum, reduce the production of IL-8, reduce neutrophil chemotaxis, and alleviate injury to airway and lung tissue; may decrease the content of TNF-α, inhibit over-activation of alveolar macrophages, reduce chemotaxis, infiltration and release of inflammatory cell, and reduce hyperreactivity of airway; may increase the content of NO in serum, lung tissue, and lavage fluid, improve the oxidation-antioxidation balance in organism, and lower the injured degree of cells in organism; may prevent the aggregation of inflammatory cell, and alleviate airway inflammation; and therefore may be used to treat airway inflammatory disease resulted from infection factors. For example, the alkaloid composition of the invention or the effective components, i.e. picrinine, vallesamine, scholaricine, and 19-epischolaricine, or any combination thereof may decrease the level of IL-6 and CRP in serum, enhance antioxidant activity in organism, reduce the infiltration of leukocyte and neutrophil, and therefore may be used to treat chronic obstructive pulmonary disease. For example, the alkaloid composition of the invention or the effective components, i.e. picrinine, vallesamine, scholaricine, and 19-epischolaricine, or any combination thereof may decrease the level of Eotaxin, IgE in serum and the content of IL-4 in bronchoalveolar lavage fluid, increase the content of IL-10 in bronchoalveolar lavage fluid, improve the oxidation-antioxidation balance in organism, reduce the infiltration of leukocyte and eosinophil, and therefore may be used to treat asthma. For example, the alkaloid composition of the invention or the effective components, i.e. picrinine, vallesamine, scholaricine, and 19-epischolaricine, or any combination thereof may decrease the level of KL-6, LDH in serum, and the content of TGF-β, Col-1, HYP and MMP-1 in homogenate, improve the oxidation-antioxidation balance in organism, and therefore may be used to treat pulmonary fibrosis disease.

Therefore, in a first aspect, the invention provides a pharmaceutical composition, comprising one or more (e.g. two, three or four) of picrinine, vallesamine, scholaricine and 19-epischolaricine.

In some preferred embodiments of the invention, the pharmaceutical composition comprises picrinine.

In some preferred embodiments of the invention, the pharmaceutical composition comprises vallesamine.

In some preferred embodiments of the invention, the pharmaceutical composition comprises scholaricine.

In some preferred embodiments of the invention, the pharmaceutical composition comprises 19-epischolaricine.

In some preferred embodiments of the invention, the pharmaceutical composition comprises picrinine and vallesamine.

In some preferred embodiments of the invention, the pharmaceutical composition comprises picrinine and scholaricine.

In some preferred embodiments of the invention, the pharmaceutical composition comprises picrinine and 19-epischolaricine.

In some preferred embodiments of the invention, the pharmaceutical composition comprises vallesamine and scholaricine.

In some preferred embodiments of the invention, the pharmaceutical composition comprises vallesamine and 19-epischolaricine.

In some preferred embodiments of the invention, the pharmaceutical composition comprises scholaricine and 19-epischolaricine.

In some preferred embodiments of the invention, the pharmaceutical composition comprises picrinine, vallesamine and scholaricine.

In some preferred embodiments of the invention, the pharmaceutical composition comprises picrinine, vallesamine and 19-epischolaricine.

In some preferred embodiments of the invention, the pharmaceutical composition comprises picrinine, scholaricine and 19-epischolaricine.

In some preferred embodiments of the invention, the pharmaceutical composition comprises vallesamine, scholaricine and 19-epischolaricine.

In some preferred embodiments of the invention, the pharmaceutical composition comprises picrinine, vallesamine, scholaricine and 19-epischolaricine.

In some preferred embodiments of the invention, the pharmaceutical composition comprises: 8-50 parts by weight of picrinine, 5-45 parts by weight of vallesamine, 5-30 parts by weight of scholaricine and 0-10 parts by weight of 19-epischolaricine.

In some preferred embodiments of the invention, in the pharmaceutical composition, picrinine is in an amount of 8-16 parts by weight.

In some preferred embodiments of the invention, in the pharmaceutical composition, vallesamine is in an amount of 5-15 parts by weight.

In some preferred embodiments of the invention, in the pharmaceutical composition, scholaricine is in an amount of 5-10 parts by weight.

In some preferred embodiments of the invention, in the pharmaceutical composition, 19-epischolaricine is in an amount of 1-5 parts by weight.

In some preferred embodiments of the invention, the pharmaceutical composition comprises: 8-16 parts by weight of picrinine, 5-15 parts by weight of vallesamine, 5-10 parts by weight of scholaricine and 1-5 parts by weight of 19-epischolaricine.

In some preferred embodiments of the invention, the pharmaceutical composition comprises: 8-12 parts by weight of picrinine, 5-9 parts by weight of vallesamine, 5-9 parts by weight of scholaricine and 1-3 parts by weight of 19-epischolaricine.

In some preferred embodiments of the invention, the pharmaceutical composition comprises about 10 parts by weight of picrinine, 7 parts by weight of vallesamine, 7 parts by weight of scholaricine and 2 parts by weight of 19-epischolaricine.

The pharmaceutical composition of the invention may be applied alone or in combination with, for example, an additional drug, such as the alkaloid composition of the invention, to form a compound, and may also be prepared in a form of health product and food through conventional procedures.

The pharmaceutical composition of the invention may be prepared into various appropriate dosage forms depending on the route of administration, by conventional procedures in the art. Therefore, in some preferred embodiments of the invention, the pharmaceutical composition further comprises a pharmaceutically acceptable carrier and/or excipient.

The pharmaceutical composition for oral use may be in the form of a tablet, a sustained-release tablet, a controlled-release tablet, a lozenge, a hard or soft capsule, an aqueous or oily suspension, an emulsion, a dispersible pulvis or granule, a syrup or elixir, a dropping pill, a mini-pill or oral solution. Therefore, a composition for oral administration may comprise, for example, one or more colouring agents, sweetening agents, flavouring agents and/or preservatives.

A pharmaceutically acceptable excipient suitable for a tablet includes an inert diluent such as lactose, sodium carbonate, calcium phosphate or calcium carbonate; a disintegrating agent such as corn starch and alginic acid; a binder, such as starch; a lubricant, such as magnesium stearate, stearic acid or talc; a preservative such as ethyl or propyl parahydroxybenzoate; and an antioxidant, such as ascorbic acid, etc. A tablet may be uncoated or coated either to modify its disintegration and the subsequent absorption of the active ingredient within the gastrointestinal tract, or to improve its stability and/or appearance. In either cases, using conventional coating agents and procedures well known in the art.

A pharmaceutically acceptable excipient suitable for a hard capsule includes an inert solid diluent such as calcium carbonate, calcium phosphate or kaolin, etc. A pharmaceutically acceptable excipient suitable for a soft capsule includes water or oil such as peanut oil, liquid paraffin or olive oil, etc.

An aqueous suspension generally comprises an active ingredient in finely powdered form together with one or more dispersants, diluents or suspending agents, the suspending agent is, for example, carboxymethylcellulose sodium, methylcellulose, hydroxypropyl methyl cellulose, sodium alginate, polyvinyl-pyrrolidone, gum tragacanth, and gum acacia, etc.; a dispersant or wetting agent, such as lecithin or a condensation product of alkylene oxide with fatty acid (e.g. polyoxyethylene stearate), or a condensation product of ethylene oxide with long-chain aliphatic alcohol, such as heptadecaethyleneoxycetanol, or a condensation product of ethylene oxide with partial ester derived from fatty acid and a hexitol, e.g. polyoxyethylene sorbitol monooleate, or a condensation product of ethylene oxide with partial ester derived from fatty acid and hexitan, e.g. polyoxyethylene sorbitan monooleate. An aqueous suspension may further comprise one or more preservatives (e.g. ethyl or propyl parahydroxybenzoate), antioxidants (e.g. ascorbic acid), colouring agents, flavouring agents, and/or sweetening agents (e.g. sucrose, saccharin and aspartame), etc.

An oily suspension may be formulated by suspending the active ingredient in a vegetable oil (such as peanut oil, olive oil, sesame oil or coconut oil) or in a mineral oil (such as liquid paraffin). The oily suspension may further comprise a thickener, such as beewax, hard paraffin, or cetyl alcohol. The sweetener and flavouring agent such as those set above may be added to provide a palatable oral preparation. These compositions may be preserved by the addition of an antioxidant such as ascorbic acid.

The pharmaceutical composition of the invention may also be in the form of oil-in-water emulsion. The oily phase may be a vegetable oil, such as olive oil or peanut oil, or a mineral oil such as liquid paraffin, or a mixture of any of these. A suitable emulsifier may be, for example, a naturally-occurring gum such as gum acacia or gum tragacanth, a naturally occurring phosphatide such as soybean lecithin, and an ester or a partial ester derived from fatty acid and hexitol anhydride (such as sorbitan monooleate), as well as a condensation product of the partial ester with ethylene oxide, such as polyoxyethylene sorbitan monooleate. An emulsion may also comprise a sweetening agent, a flavouring agent and a preservative, etc.

A syrup and an elixir may be formulated with a sweetening agent (such as glycerol, propylene glycol, sorbitol, aspartame or sucrose), or may also comprise an demulcent, a preservative, a flavouring agent and/or a colouring agent, etc.

The pharmaceutical composition for parenteral administration (e.g. intravenous administration, subcutaneous administration or intramuscular administration) may be in the form of a sterile aqueous or oily solution, an sterile powder, a liposome, an emulsion, a microemulsion, a nanoemulsion or a microcapsule.

The pharmaceutical composition may also be in the form of a sterile injectable aqueous or oily suspension, which may be formulated according to known procedures using one or more of the appropriate dispersants, diluents and/or suspending agents as described above. A sterile injectable preparation may also be a sterile injectable aqueous or oily suspension in a diluent or a solvent that is nontoxic and gastrointestinally acceptable, for example, a solution in 1,3-butanediol.

For further information on formulation the reader is referred to Chapter 25.2 in Volume 5 of Comprehensive Medicinal Chemistry (Corwin Hanschl; Chairman of Editorial Board), Pergamon Press 1990.

The amount of an active ingredient that is combined with one or more excipients to produce a single dosage form will necessarily vary depending upon the host treated and the particular route of administration. For example, a formulation intended for oral administration to human will generally comprises, for example, an active ingredient in an amount of 0.5 mg-2 g with an appropriate and convenient amount of excipient (which accounts for about 5-98% of the total weight of a composition). Dosage unit form will generally comprise an active ingredient in an amount of about 1 mg-500 mg. For further information on routes of administration and dosage regimes the reader is referred to Chapter 25.3 in Volume 5 of Comprehensive Medicinal Chemistry (Corwin Hanschl; Chairman of Editorial Board), Pergamon Press 1990.

The size of the dose for therapeutic or prophylactic purposes of the pharmaceutical composition will naturally vary according to the nature and severity of the conditions, the age and gender of the animal or patient, and the route of administration, etc.

In using a pharmaceutical composition for therapeutic or prophylactic purpose it will generally be administered so that a daily dose in the range, for example, 1 mg-100 mg/kg body weight is received, given if required in divided doses. In general, lower doses will be administered when a parenteral route is employed. Thus, for example, for intravenous administration, a dose in a range, for example, 1 mg-10 mg/kg body weight will generally be used.

In a second aspect, the invention provides an alkaloid composition extracted from leaves of *Alstonia scholaris*, comprising: 8-50 parts by weight of picrinine, 5-45 parts by weight of vallesamine, 5-30 parts by weight of scholaricine and 0-10 parts by weight of 19-epischolaricine.

In some preferred embodiments of the invention, picrinine is in an amount of 8-16 parts by weight.

In some preferred embodiments of the invention, vallesamine is in an amount of 5-15 parts by weight.

In some preferred embodiments of the invention, scholaricine is in an amount of 5-10 parts by weight.

In some preferred embodiments of the invention, 19-epischolaricine is in an amount of 1-5 parts by weight.

In some preferred embodiments of the invention, the alkaloid composition comprises: 8-16 parts by weight of picrinine, 5-15 parts by weight of vallesamine, 5-10 parts by weight of scholaricine and 1-5 parts by weight of 19-epischolaricine.

In some preferred embodiments of the invention, the alkaloid composition comprises: 8-12 parts by weight of picrinine, 5-9 parts by weight of vallesamine, 5-9 parts by weight of scholaricine and 1-3 parts by weight of 19-epischolaricine.

In some preferred embodiments of the invention, the alkaloid composition comprises about 10 parts by weight of picrinine, 7 parts by weight of vallesamine, 7 parts by weight of scholaricine and 2 parts by weight of 19-epischolaricine.

In a third aspect, the invention provides an alkaloid composition extracted from leaves of *Alstonia scholaris*, which is prepared by the following method:

Method 1:

leaves of *Alstonia scholaris* are extracted with ethanol or an ethanol aqueous solution, and the extract is collected and concentrated to obtain a concrete; the concrete is soaked with hydrochloric acid or sulfuric acid for 1-5 times (e.g. 1, 2, 3, 4 or 5 times), filtrated, to collect a filtrate; the filtrate is loaded to an ion exchange resin, and eluted with water and ethanol-ammonia water, respectively; the eluent eluted by the ethanol-ammonia water is collected and concentrated to obtain the alkaloid composition; or, Method 2:

(1) leaves of *Alstonia scholaris* are extracted with ethanol or an ethanol aqueous solution, and the extract is collected and concentrated to obtain a concrete; the concrete is soaked with hydrochloric acid or sulfuric acid, and filtrated; the filtrate is collected and concentrated, to obtain an acidic ethanol extract;

(2) the acidic ethanol extract is dissolved in water, adjusted to have a basic pH, and extracted with ethyl acetate, the ethyl acetate phase is collected and concentrated, to obtain the alkaloid composition.

In some preferred embodiments of the invention, the method is characterized by one or more of the following items:

(1) in Method 1 or Method 2, each kilogram of leaves of *Alstonia scholaris* is extracted with 1-20 liters (e.g. 5 liters, 10 liters, 15 liters) of ethanol or an ethanol aqueous solution;

(2) in Method 1 or Method 2, the ethanol aqueous solution has a mass fraction of 50-95%, e.g. a mass fraction of 60%, 70%, 80% or 90%;

(3) in Method 1 or Method 2, leaves of *Alstonia scholaris* are extracted under heating, for example, at 50-100° C. (e.g. 60° C., 70° C., 80° C. or 90° C.), for example, at reflux;

(4) in Method 1 or Method 2, the hydrochloric acid has a mass fraction of 0.1-20% (e.g. 0.1-10% hydrochloric acid, e.g. 0.1-5% hydrochloric acid, e.g. 0.1-1% hydrochloric acid, e.g. 0.3% hydrochloric acid, e.g. 0.4% hydrochloric acid, e.g. 0.05% hydrochloric acid);

(5) in Method 1 or Method 2, the sulfuric acid has a mass fraction of 0.01-10% (e.g. 0.01-5% sulfuric acid, e.g. 0.01-1% sulfuric acid, e.g. 0.01-0.05% sulfuric acid, e.g. 0.02% sulfuric acid, e.g. 0.04% sulfuric acid);

(6) in Method 1 or Method 2, the hydrochloric acid or sulfuric acid is used in such an amount that the filtrate has an acidic pH, for example, has a pH of 2-6 (e.g. 2.5, 3, 3.5, 4, 4.5, 5 or 5.5);

(7) in Method 1, before loading the filtrate to the ion exchange resin, a step of concentrating the filtrate is further comprised;

(8) in Method 1, the ion exchange resin is a cation exchange resin, e.g. LSD001 Type cation exchange resin, e.g. 001×7 Type cation exchange resin, e.g. 001×4 Type cation exchange resin;

(9) in Method 1, ethanol and ammonia water is in a volume ratio of is (1-10):1, e.g. (1-5): 1, e.g. 1:1, e.g. 2:1, e.g. 3:1, e.g. 4:1, e.g. 5:1 in the ethanol-ammonia water;

(10) in step (2) of Method 2, each kilogram of the acidic ethanol extract is dissolved with water in an amount of 1-15 L, e.g. 3-15 L, e.g. 5 L, e.g. 7 L, e.g. 10 L, e.g. 12 L;

(11) in step (2) of Method 2, the pH is adjusted by a base (e.g. ammonia water (e.g. 20% ammonia water), NaOH aqueous solution (e.g. 10% NaOH aqueous solution), KOH aqueous solution (e.g. 10% KOH aqueous solution) or $Na_2CO_3$ aqueous solution (e.g. 30% $Na_2CO_3$ aqueous solution));

(12) in step (2) of Method 2, the pH value is 7.5-11 (e.g. 8, 8.5, 9, 9.5, 10, 10.5 or 11).

In another aspect, the invention provides use of the pharmaceutical composition of the first aspect, the alkaloid composition of the second aspect or the third aspect, or picrinine, vallesamine, scholaricine, 19-epischolaricine or any combination thereof in the manufacture of a medicament for treating a respiratory disease.

In some preferred embodiments of the invention, the respiratory disease is selected from airway inflammation, chronic obstructive pulmonary disease, asthma and pulmonary fibrosis disease.

In some preferred embodiments of the invention, the pharmaceutical composition, alkaloid composition, picrinine, vallesamine, scholaricine, 19-epischolaricine or any combination thereof is administered in a daily dose of 1 mg-100 mg/kg.

In another aspect, the invention provides use of the pharmaceutical composition of the first aspect, the alkaloid composition of the second aspect or the third aspect, or picrinine, vallesamine, scholaricine, 19-epischolaricine or any combination thereof in the manufacture of a medicament for lowering the number of inflammatory cell in lung tissue.

In some preferred embodiments of the present application, the inflammatory cell is selected from leukocyte and neutrophil.

In another aspect, the invention provides use of the pharmaceutical composition of the first aspect, the alkaloid composition of the second aspect or the third aspect, or picrinine, vallesamine, scholaricine, 19-epischolaricine or any combination thereof in the manufacture of a medicament for decreasing the level of IL-8 and TNF-α in a cell, or increasing the level of NO in a cell, or treating a disease or disorder caused by abnormal content of IL-8, TNF-α and/or NO in a cell.

In some preferred embodiments of the invention, the disease or disorder caused by abnormal content of IL-8, TNF-α and/or NO in a cell is airway inflammation.

In another aspect, the invention provides use of the pharmaceutical composition of the first aspect, the alkaloid composition of the second aspect or the third aspect, or picrinine, vallesamine, scholaricine, 19-epischolaricine or any combination thereof in the manufacture of a medicament for decreasing the level of IL-6 and/or CRP in a cell or treating a disease or disorder caused by abnormal content of IL-6 and/or CRP in a cell.

In some preferred embodiments of the invention, the disease or disorder caused by abnormal content of IL-6 and/or CRP in a cell is chronic obstructive pulmonary disease.

In another aspect, the invention provides use of the pharmaceutical composition of the first aspect, the alkaloid composition of the second aspect or the third aspect, or picrinine, vallesamine, scholaricine, 19-epischolaricine or any combination thereof in the manufacture of a medicament for decreasing the level of Eotaxin, IgE and/or IL-4 in a cell, increasing the level of IL-10 in a cell, or treating a disease or disorder caused by abnormal content of Eotaxin, IgE, IL-4 and/or IL-10 in a cell.

In some preferred embodiments of the invention, the disease or disorder caused by abnormal content of Eotaxin, IgE, IL-4 and/or IL-10 in a cell is asthma.

In another aspect, the invention provides use of the pharmaceutical composition of the first aspect, the alkaloid composition of the second aspect or the third aspect, or picrinine, vallesamine, scholaricine, 19-epischolaricine or any combination thereof in the manufacture of a medicament for decreasing the level of KL-6, LDH, TGF-β, Col-1, Hyp and/or MMP-1 in a cell or treating a disease or disorder caused by abnormal content of KL-6, LDH, TGF-β, Col-1, Hyp and/or MMP-1 in a cell.

In some preferred embodiments of the invention, the disease or disorder caused by abnormal content of KL-6, LDH, TGF-β, Col-1, Hyp and/or MMP-1 in a cell is pulmonary fibrosis disease.

In another aspect, the invention provides use of the pharmaceutical composition of the first aspect, the alkaloid composition of the second aspect or the third aspect, or picrinine, vallesamine, scholaricine, 19-epischolaricine or any combination thereof in the manufacture of a medicament for increasing the level of SOD in a cell, decreasing the level of MDA in a cell, or treating a disease or disorder caused by abnormal content of SOD and/or MDA.

In some preferred embodiments of the invention, the disease or disorder caused by abnormal content of SOD and/or MDA is selected from airway inflammation, chronic obstructive pulmonary disease, asthma and pulmonary fibrosis disease.

In another aspect, the invention provides a method for treating a respiratory disease, comprising administering to a subject in need thereof an effective amount of the pharmaceutical composition of the first aspect of the invention, the alkaloid composition of the second aspect or the third aspect, or picrinine, vallesamine, scholaricine, 19-epischolaricine or any combination thereof.

In some preferred embodiments of the invention, the respiratory disease is selected from airway inflammation, chronic obstructive pulmonary disease, asthma and pulmonary fibrosis disease.

In another aspect, the invention provides a method for decreasing the number of inflammatory cell in lung tissue, comprising administering to a subject in need thereof the pharmaceutical composition of the first aspect of the invention or the alkaloid composition of leaves of *Alstonia scholaris* of the second aspect or the third aspect.

In some preferred embodiments of the present application, the inflammatory cell is selected from leukocyte and neutrophil.

In another aspect, the invention provides a method for decreasing the level of IL-8 and TNF-α in a cell, or increasing the level of NO in a cell, or treating a disease or disorder caused by abnormal content of IL-8, TNF-α and/or NO in a cell, comprising administering to a cell or a subject in need thereof the pharmaceutical composition of the first aspect of the invention, the alkaloid composition of the second aspect or the third aspect, or picrinine, vallesamine, scholaricine, 19-epischolaricine or any combination thereof.

In some preferred embodiments of the invention, the disease or disorder caused by abnormal content of IL-8, TNF-α and/or NO in a cell is airway inflammation.

In another aspect, the invention provides a method for decreasing the level of IL-6 and/or CRP in a cell or treating a disease or disorder caused by abnormal content of IL-6 and/or CRP in a cell, comprising administering to a cell or a subject in need thereof an effective amount of the pharmaceutical composition of the first aspect, the alkaloid composition of the second aspect or the third aspect, or picrinine, vallesamine, scholaricine, 19-epischolaricine or any combination thereof.

In some preferred embodiments of the invention, the disease or disorder caused by abnormal content of IL-6 and/or CRP in a cell is chronic obstructive pulmonary disease.

In another aspect, the invention provides a method for decreasing the level of Eotaxin, IgE and/or IL-4 in a cell, increasing the level of IL-10 in a cell, or treating a disease or disorder caused by abnormal content of Eotaxin, IgE, IL-4 and/or IL-10 in a cell, comprising administering to a cell or a subject in need thereof an effective amount of the pharmaceutical composition of the first aspect of the invention, the alkaloid composition of the second aspect or the third aspect, or picrinine, vallesamine, scholaricine, 19-epischolaricine or any combination thereof.

In some preferred embodiments of the invention, the disease or disorder caused by abnormal content of Eotaxin, IgE, IL-4 and/or IL-10 in a cell is asthma.

In another aspect, the invention provides a method for decreasing the level of KL-6, LDH, TGF-β, Col-1, Hyp and/or MMP-1 in a cell or treating a disease or disorder caused by abnormal content of KL-6, LDH, TGF-β, Col-1, Hyp and/or MMP-1 in a cell, comprising administering to a cell or a subject in need thereof an effective amount of the pharmaceutical composition of the first aspect of the invention, the alkaloid composition of the second aspect or the third aspect, or picrinine, vallesamine, scholaricine, 19-epischolaricine or any combination thereof.

In some preferred embodiments of the invention, the disease or disorder caused by abnormal content of KL-6, LDH, TGF-β, Col-1, Hyp and/or MMP-1 in a cell is pulmonary fibrosis disease.

In another aspect, the invention provides a method for increasing the level of SOD in a cell, decreasing the level of MDA in a cell, or treating a disease or disorder caused by abnormal content of SOD and/or MDA, comprising administering to a cell or a subject in need thereof an effective amount of the pharmaceutical composition of the first aspect of the invention, the alkaloid composition of the second aspect or the third aspect, or picrinine, vallesamine, scholaricine, 19-epischolaricine or any combination thereof.

In some preferred embodiments of the invention, the disease or disorder caused by abnormal content of SOD and/or MDA is respiratory disease.

In another aspect, the invention provides the pharmaceutical composition of the first aspect, the alkaloid composition of the second aspect or the third aspect, or picrinine, vallesamine, scholaricine, 19-epischolaricine or any combination thereof, for use in treating a respiratory disease.

In some preferred embodiments of the invention, the respiratory disease is selected from airway inflammation, chronic obstructive pulmonary disease, asthma and pulmonary fibrosis disease.

In another aspect, the invention provides the pharmaceutical composition of the first aspect, the alkaloid composition of the second aspect or the third aspect, or picrinine, vallesamine, scholaricine, 19-epischolaricine or any combination thereof, for use in lowering the number of inflammatory cell in lung tissue.

In some preferred embodiments of the present application, the inflammatory cell is selected from leukocyte and neutrophil.

In another aspect, the invention provides the pharmaceutical composition of the first aspect, the alkaloid composition of the second aspect or the third aspect, or picrinine, vallesamine, scholaricine, 19-epischolaricine or any combination thereof, for use in decreasing the level of IL-8 and TNF-α in a cell, or increasing the level of NO in a cell, or treating a disease or disorder caused by abnormal content of IL-8, TNF-α and/or NO in a cell.

In some preferred embodiments of the invention, the disease or disorder caused by abnormal content of IL-8, TNF-α and/or NO in a cell is airway inflammation.

In another aspect, the invention provides the pharmaceutical composition of the first aspect, the alkaloid composition of the second aspect or the third aspect, or picrinine, vallesamine, scholaricine, 19-epischolaricine or any combination thereof, for use in decreasing the level of IL-6 and/or CRP in a cell or treating a disease or disorder caused by abnormal content of IL-6 and/or CRP in a cell.

In some preferred embodiments of the invention, the disease or disorder caused by abnormal content of IL-6 and/or CRP in a cell is chronic obstructive pulmonary disease.

In another aspect, the invention provides the pharmaceutical composition of the first aspect, the alkaloid composition of the second aspect or the third aspect, or picrinine, vallesamine, scholaricine, 19-epischolaricine or any combination thereof, for use in decreasing the level of Eotaxin, IgE and/or IL-4 in a cell, increasing the level of IL-10 in a cell, or treating a disease or disorder caused by abnormal content of Eotaxin, IgE, IL-4 and/or IL-10 in a cell.

In some preferred embodiments of the invention, the disease or disorder caused by abnormal content of Eotaxin, IgE, IL-4 and/or IL-10 in a cell is asthma.

In another aspect, the invention provides the pharmaceutical composition of the first aspect, the alkaloid composition of the second aspect or the third aspect, or picrinine, vallesamine, scholaricine, 19-epischolaricine or any combination thereof, for use in decreasing the level of KL-6, LDH, TGF-β, Col-1, Hyp and/or MMP-1 in a cell or treating a disease or disorder caused by abnormal content of KL-6, LDH, TGF-β, Col-1, Hyp and/or MMP-1 in a cell.

In some preferred embodiments of the invention, the disease or disorder caused by abnormal content of KL-6, LDH, TGF-β, Col-1, Hyp and/or MMP-1 in a cell is pulmonary fibrosis disease.

In another aspect, the invention provides the pharmaceutical composition of the first aspect, the alkaloid composition of the second aspect or the third aspect, or picrinine, vallesamine, scholaricine, 19-epischolaricine or any combination thereof, for use in increasing the level of SOD in a cell, decreasing the level of MDA in a cell, or treating a disease or disorder caused by abnormal content of SOD and/or MDA.

In some preferred embodiments of the invention, the disease or disorder caused by abnormal content of SOD and/or MDA is a respiratory disease.

In some preferred embodiments of the invention, the respiratory disease is selected from airway inflammation, chronic obstructive pulmonary disease, asthma and pulmonary fibrosis disease.

In the invention, the "airway inflammation" refers to upper airway (mainly including nose, pharynx and larynx) and lower airway (mainly including trachea) inflammatory disease, which is one of the common and frequently-occurring respiratory diseases in clinic, mainly including bronchial asthma, chronic obstructive pulmonary disease, interstitial pneumonia, etc., which often co-exist at the same time. It is selected from disease of airway inflammation resulted from any of the following causes: smoking, infection, air pollution, harmful gas, dust inhalation, intrinsic factor of organism, etc.

In the invention, the chronic obstructive pulmonary disease is resulted from any of the following causes: smoking, infection, physical and chemical factor, and air pollution.

In the invention, the physical and chemical factor refers to physical, chemical or biological factor that has an effect on a disease; wherein a physical factor includes high temperature, low temperature, low atmospheric pressure, high atmospheric pressure, noise, vibration, ionizing radiation, high frequency, ultraviolet light, snow blinding, electric shock, drowning, seasickness, etc.; chemical factors include, for example, "three wastes" in industry, organic solvents, irritating gases, asphyxiating toxicants, corrosive toxicants, heavy metal ions, agricultural chemicals, and the like, as well as household cleaners, pesticides, drugs, etc.

In the invention, the asthma is resulted from any of the following causes: food, dust mite, pollen, fungal spore, animal scurf, insect excrement, drug, and cold air.

In the invention, the pulmonary fibrosis disease is resulted from any of the following causes: smoking, asbestos, inorganic dust, drug, radiation injury, harmful gas, infection, environmental factor and pneumopathy.

In the invention, the term "subject" refers to animal, particularly mammal, preferably human.

In the invention, the term "an effective amount" refers to an amount that is sufficient to achieve or at least partially achieve a desired effect. For example, a prophylactically effective amount refers to an amount that is sufficient to prevent, suppress or delay the occurrence of a disease; a therapeutically effective amount refers to an amount that is sufficient to cure or at least partially suppress a disease and its complications in a patient with the disease. The determination of such an effective amount is completely within the ability of a person skilled in the art. For example, an amount effective for a therapeutic use depends on the severity degree of a disease to be treated, general state of the immune system in a patient, general conditions of a patient such as age, weight and gender, route of administration of the drug, additional therapies used simultaneously, and the like.

In the invention, the particular amount of the effective components in the pharmaceutical composition or alkaloid composition is expressed by using "about". It means that due to the objective reasons such as analytic means or instrumental error, the actual amount of the effective monomer may be in the range of the numerical value of the present application ±20%, e.g. ±10%, e.g. ±5%, e.g. ±2%, e.g. ±1%, e.g. ±0.5%, e.g. ±0.1%.

The pharmaceutical composition of the invention may be prepared by the following method: an alkaloid composition comprising the components or pure form of the components is prepared by any known method, and then the pharmaceutical composition and the pure form of the components are mixed so that the components are present in a desired ratio. For example, picrinine used may be an alkaloid composition comprising 10-99% picrinine or a pure form of picrinine, preferably an alkaloid composition extracted from a plant of the family Apocynaceae, more preferably an alkaloid composition extracted from a plant of the genus *Alstonia*, more preferably an alkaloid composition of *Alstonia scholaris* comprising 10-99% picrinine. Vallesamine used may be an alkaloid composition comprising 10-99% vallesamine or a pure form of vallesamine, preferably an alkaloid composition extracted from a plant of the family Apocynaceae, more preferably an alkaloid composition extracted from a plant of the genus *Alstonia*, more preferably an alkaloid composition of *Alstonia scholaris* comprising 10-99% vallesamine. Scholaricine used may be an alkaloid composition comprising 10-99% scholaricine or a pure form of scholaricine, preferably an alkaloid composition extracted from a plant of the family Apocynaceae, more preferably an alkaloid composition extracted from a plant of the genus *Alstonia*, more preferably an alkaloid composition of *Alstonia scholaris* comprising 10-99% scholaricine. 19-epischolaricine used may be an alkaloid composition comprising 10-99% 19-epischolaricine or a pure form of 19-epischolaricine, preferably an alkaloid composition extracted from a plant of the family Apocynaceae, more preferably an alkaloid composition comprising extracted from a plant of the genus *Alstonia*, more preferably an alkaloid composition of *Alstonia scholaris* comprising 10-99% 19-epischolaricine.

In another aspect, the invention provides a method for preparing the pharmaceutical composition of the first aspect, characterized in that, the method comprises the following steps:

a. *Alstonia scholaris* is used as raw material to prepare the alkaloid composition, b. optionally, according to actual need, the alkaloid composition is mixed with at least one of a pure form of picrinine, vallesamine, scholaricine or 19-epischolaricine, or an alkaloid composition comprising picrinine, vallesamine, scholaricine and 19-epischolaricine in any ratio, so that in the pharmaceutical composition, picrinine, vallesamine, scholaricine, and 19-epischolaricine are present in the amounts by weight as required in the pharmaceutical composition of the first aspect of the invention.

In some preferred embodiments of the invention, step a comprises: *Alstonia scholaris* is used as raw material, and is subjected to reflux extraction with aqueous ethanol; the extract is concentrated and soaked with an aqueous solution of acid (preferably hydrochloric acid or sulfuric acid), and filtrated; the resultant acidic aqueous solution is concentrated to obtain an acidic ethanol extract; the acidic ethanol extract is dissolved in water, and adjusted with a base (preferably, ammonia water, NaOH, KOH or $Na_2CO_3$ aqueous solution) to have a pH of 7.5-11; the resultant solution is extracted with ethyl acetate, and the solvent is recovered from the organic phase, to obtain the alkaloid composition.

In some preferred embodiments of the invention, the method is characterized by one or more of the following items:

(1) in step a, the raw material is selected from bark, root and leaf of *Alstonia scholaris*, preferably, leaf of *Alstonia scholaris*;

(2) in step a, 1-20 liters (e.g. 5 liters, 10 liters, 15 liters) of aqueous ethanol are used to extract each kilogram of *Alstonia scholaris*;

(3) in step a, the aqueous ethanol has a mass fraction of 50-95%, e.g. a mass fraction of 60%, 70%, 80% or 90%;

(4) in step a, the extraction is performed under heating, for example, the extraction is performed at 50-100° C. (e.g. 60° C., 70° C., 80° C. or 90° C.), for example, the extraction is performed at reflux;

(5) in step a, the concentrated aqueous ethanol extract is soaked with hydrochloric acid with a mass fraction of 0.1-20% (e.g. 0.1-10% hydrochloric acid, e.g. 0.1-5% hydrochloric acid, e.g. 0.1-1% hydrochloric acid, e.g. 0.3% hydrochloric acid, e.g. 0.4% hydrochloric acid, e.g. 0.05% hydrochloric acid);

(6) in step a, the concentrated aqueous ethanol extract is soaked with sulfuric acid with a mass fraction of 0.01-10% (e.g. 0.01-5% sulfuric acid, e.g. 0.01-1% sulfuric acid, e.g. 0.01-0.05% sulfuric acid, e.g. 0.02% sulfuric acid, e.g. 0.04% sulfuric acid);

(7) in step a, each kilogram of the acidic ethanol extract is dissolved with water in an amount of 1-15 L, e.g. 3-15 L, e.g. 5 L, e.g. 7 L, e.g. 10 L, e.g. 12 L;

(8) in step a, the pH is adjusted with a base (e.g. ammonia water (e.g. 20% ammonia water), NaOH aqueous solution (e.g. 10% NaOH aqueous solution), KOH aqueous solution (e.g. 10% KOH aqueous solution) or $Na_2CO_3$ aqueous solution (e.g. 30% $Na_2CO_3$ aqueous solution));

(9) in step a, a base is used to adjust pH to 7.5-11 (e.g. 8, 8.5, 9, 9.5, 10, 10.5 or 11).

In some preferred embodiments of the invention, step a comprises: *Alstonia scholaris* is used as raw material, and is subjected to reflux extraction with aqueous ethanol, the extract is concentrated and soaked with an aqueous solution of acid (preferably hydrochloric acid or sulfuric acid), and filtrated; the resultant acidic aqueous solution is concentrated to obtain an acidic ethanol extract; the acidic ethanol extract is dissolved in water, and pH is adjusted with an acid (preferably hydrochloric acid or sulfuric acid) to 2-6; the resultant solution is loaded to an ion exchange resin, and eluted with water and ethanol-ammonia water, respectively; the eluent eluted by the ethanol-ammonia water is collected, and the solvent is recovered, to obtain an alkaloid composition. In some preferred embodiments of the invention, the method is characterized by one or more of the following items:

(1) in step a, the raw material is selected from bark, root and leaf of *Alstonia scholaris*, preferably, leaf of *Alstonia scholaris*;

(2) in step a, 1-20 liters (e.g. 5 liters, 10 liters, 15 liters) of aqueous ethanol are used to extract each kilogram of *Alstonia scholaris*;

(3) in step a, the aqueous ethanol has a mass fraction of 50-95%, e.g. a mass fraction of 60%, 70%, 80% or 90%;

(4) in step a, the extraction is performed under heating, for example, the extraction is performed at 50-100° C. (e.g. 60° C., 70° C., 80° C. or 90° C.), for example, the extraction is performed at reflux;

(5) in step a, the concentrated aqueous ethanol extract is soaked with hydrochloric acid with a mass fraction of 0.1-20% (e.g. 0.1-10% hydrochloric acid, e.g. 0.1-5% hydrochloric acid, e.g. 0.1-1% hydrochloric acid, e.g. 0.3% hydrochloric acid, e.g. 0.4% hydrochloric acid, e.g. 0.05% hydrochloric acid);

(6) in step a, the concentrated aqueous ethanol extract is soaked with sulfuric acid with a mass fraction of 0.01-10% (e.g. 0.01-5% sulfuric acid, e.g. 0.01-1% sulfuric acid, e.g. 0.01-0.05% sulfuric acid, e.g. 0.02% sulfuric acid, e.g. 0.04% sulfuric acid);

(7) in step a, each kilogram of the acidic ethanol extract is dissolved with water in an amount of 1-15 L, e.g. 3-15 L, e.g. 5 L, e.g. 7 L, e.g. 10 L, e.g. 12 L;

(8) in step a, an acid is used to adjust the pH of the aqueous solution of the acidic ethanol extract to an acidic pH, e.g. pH of 2-6 (e.g. 2.5, 3, 3.5, 4, 4.5, 5 or 5.5);

(9) in step a, the ion exchange resin is a cation exchange resin, e.g. LSD001 Type cation exchange resin, e.g. 001×7 Type cation exchange resin, e.g. 001×4 Type cation exchange resin;

(10) in step a, ethanol and ammonia water is in a volume ratio of is (1-10):1, e.g. (1-5): 1, e.g. 1:1, e.g. 2:1, e.g. 3:1, e.g. 4:1, e.g. 5:1 in the ethanol-ammonia water.

The pharmaceutical composition of the invention has a simple preparation process and is easily to obtained, thus showing high clinically applicable prospect.

In another aspect, the invention provides a method for preparing an alkaloid composition extracted from leaves of *Alstonia scholaris*, which is selected from Method 1 and Method 2, Method 1:

leaves of *Alstonia scholaris* are extracted with ethanol or an ethanol aqueous solution, and the extract is collected and concentrated to obtain a concrete; the concrete is soaked with hydrochloric acid or sulfuric acid for 1-5 times (e.g. 1, 2, 3, 4 or 5 times), and filtrated to collect a filtrate; the filtrate is loaded to an ion exchange resin, and eluted with water and ethanol-ammonia water, respectively; the eluent eluted by the ethanol-ammonia water is collected and concentrated, to obtain the alkaloid composition; or, Method 2:

(1) leaves of *Alstonia scholaris* are extracted with ethanol or an ethanol aqueous solution, and the extract is collected and concentrated to obtain a concrete; the concrete is soaked with hydrochloric acid or sulfuric acid, and filtrated; the filtrate is collected and concentrated, to obtain an acidic ethanol extract;

(2) the acidic ethanol extract is dissolved in water, adjusted to have a basic pH, and extracted with ethyl acetate, the ethyl acetate phase is collected and concentrated, to obtain the alkaloid composition.

In some preferred embodiments of the invention, the method is characterized by one or more of the following items:

(1) in Method 1 or Method 2, 1-20 liters (e.g. 5 liters, 10 liters, 15 liters) of ethanol or an ethanol aqueous solution are used to extract each kilogram of leaves of *Alstonia scholaris*;

(2) in Method 1 or Method 2, the ethanol aqueous solution has a mass fraction of 50-95%, e.g. a mass fraction of 60%, 70%, 80% or 90%;

(3) in Method 1 or Method 2, leaves of *Alstonia scholaris* are extracted under heating, for example, at 50-100° C. (e.g. 60° C., 70° C., 80° C. or 90° C.), for example, at reflux;

(4) in Method 1 or Method 2, the hydrochloric acid has a mass fraction of 0.1-20% (e.g. 0.1-10% hydrochloric acid, e.g. 0.1-5% hydrochloric acid, e.g. 0.1-1% hydrochloric acid, e.g. 0.3% hydrochloric acid, e.g. 0.4% hydrochloric acid, e.g. 0.05% hydrochloric acid);

(5) in Method 1 or Method 2, the sulfuric acid has a mass fraction of 0.01-10% (e.g. 0.01-5% sulfuric acid, e.g. 0.01-1% sulfuric acid, e.g. 0.01-0.05% sulfuric acid, e.g. 0.02% sulfuric acid, e.g. 0.04% sulfuric acid);

(6) in Method 1 or Method 2, the hydrochloric acid or sulfuric acid is used in such an amount that the filtrate has an acidic pH, for example, has a pH of 2-6 (e.g. 2.5, 3, 3.5, 4, 4.5, 5 or 5.5);

(7) in Method 1, before loading the filtrate to the ion exchange resin, a step of concentrating the filtrate is further comprised;

(8) in Method 1, the ion exchange resin is cation exchange resin, e.g. LSD001 Type cation exchange resin, e.g. 001×7 Type cation exchange resin, e.g. 001×4 Type cation exchange resin;

(9) in Method 1, ethanol and ammonia water is in a volume ratio of is (1-10):1, e.g. (1-5): 1, e.g. 1:1, e.g. 2:1, e.g. 3:1, e.g. 4:1, e.g. 5:1 in the ethanol-ammonia water;

(10) in step (2) of Method 2, each kilogram of the acidic ethanol extract is dissolved with water in an amount of 1-15 L, e.g. 3-15 L, e.g. 5 L, e.g. 7 L, e.g. 10 L, e.g. 12 L;

(11) in step (2) of Method 2, the pH is adjusted by a base (e.g. ammonia water (e.g. 20% ammonia water), NaOH aqueous solution (e.g. 10% NaOH aqueous solution), KOH aqueous solution (e.g. 10% KOH aqueous solution) or $Na_2CO_3$ aqueous solution (e.g. 30% $Na_2CO_3$ aqueous solution));

(12) in step (2) of Method 2, the pH value is 7.5-11 (e.g. 8, 8.5, 9, 9.5, 10, 10.5 or 11).

In another aspect, the invention further provides use of the pharmaceutical composition of the first aspect of the invention or the alkaloid composition of the second aspect or the third aspect of the invention in the manufacture of a medicament for treating airway inflammatory disease resulted from any of infection factor.

In some preferred embodiments of the invention, the pharmaceutical composition or alkaloid composition is administered in a daily dose of 1 mg-100 mg/kg/d, which may be used to suppress aggregation of inflammatory cell, and alleviate airway inflammation.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of IL-8 in lung tissue, wherein the pharmaceutical composition or alkaloid composition may decrease the level of IL-8 in BALF, lung tissue, and serum, reduce the production of IL-8, reduce neutrophil chemotaxis, and alleviate the injury to airway and lung tissue.

In another aspect, the invention further provides use of the pharmaceutical composition of the first aspect of the invention or the alkaloid composition of the second aspect or the third aspect of the invention in the manufacture of a medicament for a disease or disorder caused by abnormal content of TNF-α in lung tissue, wherein the pharmaceutical composition or alkaloid composition can inhibit over-activation of alveolar macrophages, reduce chemotaxis, infiltration and release of inflammatory cell, and reduce hyperreactivity of airway by decreasing the content of TNF-α.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of NO in lung tissue, wherein the pharmaceutical composition or alkaloid composition may increase the content of NO in lung tissue and lavage fluid, improve the oxidation-antioxidation balance in organism, and lower the injured degree of cell in organism.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of IL-6 in lung tissue, wherein the pharmaceutical composition or alkaloid composition may decrease the level of IL-6 in serum, reduce the production of IL-6, alleviate the occurrence and development of local inflammation, and alleviate the remodeling of airway structure and formation of airway obstruction.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of CRP in serum, wherein the pharmaceutical composition or alkaloid composition may inhibit over-activation of alveolar macrophages, reduce chemotaxis, infiltration and release of inflammatory cell, and alleviate airway inflammation, by decreasing the content of CRP.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of Eotaxin in serum, wherein the pharmaceutical composition or alkaloid composition may inhibit over-activation of alveolar eosinophil, reduce chemotaxis, infiltration and release of eosinophil, and alleviate symptom of asthma, by decreasing the content of Eotaxin in serum.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of IgE in serum, wherein the pharmaceutical composition or alkaloid composition may alleviate the occurrence of allergy and alleviate symptom of asthma by reducing the production of IgE in serum.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of IL-4 in lavage fluid, wherein the pharmaceutical composition or alkaloid composition may inhibit the production of immunoglobulin, reduce chemotaxis, infiltration and release of eosinophil, and alleviate symptom of asthma, by decreasing the level of IL-4.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of IL-10 in lavage fluid, wherein the pharmaceutical composition or alkaloid composition can inhibit the production of immunoglobulin, reduce chemotaxis, infiltration and release of eosinophil, inhibit the degree of inflammation, and alleviate symptom of asthma, by increasing the level of IL-10.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of KL-6 in serum, wherein the pharmaceutical composition or alkaloid composition may alleviate the injury of alveolar epithelial cell and the injured degree of lung tissue blood-air barrier function, and have a preventive and therapeutic effect on pulmonary fibrosis, by decreasing the expression of KL-6.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of LDH in serum, wherein the pharmaceutical composition or alkaloid composition may alleviate the injury of alveolar epithelial cell and the injured degree of lung tissue blood-air barrier function, and have a preventive and therapeutic effect on pulmonary fibrosis, by decreasing the content of LDH.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of TGF-β in tissue, wherein the pharmaceutical composition or alkaloid composition may reduce the production of TGF-β in lung tissue, lower the degree of fibrosis, and have a protective effect on lung tissue.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of Col-1 in tissue, wherein the pharmaceutical composition or alkaloid composition may reduce the production of Col-1 in lung tissue, reduce the formation of collagen, and reduce fibrosis.

In another aspect, the invention further provides use of the pharmaceutical composition of the first aspect of the invention or the alkaloid composition of the second aspect or the third aspect of the invention in the manufacture of a medicament for treating a disease or disorder caused by abnormal content of Hyp in tissue, wherein the pharmaceutical composition or alkaloid composition may reduce the production of Hyp in lung tissue, reduce the formation of collagen, and reduce fibrosis.

In some embodiments of the invention, the pharmaceutical composition or alkaloid composition of the invention may clean the injury of free radical to organism, and maintain the balance of free radical generation and clearance; repair injured pulmonary alveolar epithelial-capillary barrier, and repair injured alveolar type II epithelial cell and other cells.

In some embodiments of the invention, the pharmaceutical composition or alkaloid composition of the invention may reduce MDA in serum and BALF, significantly improve oxidization-antioxidization balance in vivo, and lower the injured degree of cells in organism; significantly increase LDH in bronchoalveolar lavage fluid and serum, lower the injured degree of cells, significantly reduce the number and degree of pathological changes, and resist histomorphological changes of airway inflammation.

In some embodiments of the invention, the pharmaceutical composition or alkaloid composition of the invention may decrease IL-6 and CRP in serum, significantly inhibit over-activation of alveolar macrophages, reduce chemotaxis, infiltration and release of inflammatory cell, alleviate the occurrence and development of local inflammation, and alleviate the remodeling of airway structure and formation of airway obstruction.

In the invention, in vivo pharmacodynamic studies on the pharmaceutical composition or alkaloid composition were conducted. The results showed: after intragastrical administration for 5 days continuously, the pharmaceutical composition or alkaloid composition significantly inhibit the aggregation of inflammatory cell in infectious airway inflammation duplicated by lipopolysaccharide, decrease the level of IL-8, TNF-α, enhance the activity of NO and SOD, decrease the content of MDA, alleviate the injury of pulmonary alveolar epithelial-capillary barrier, and alleviate airway inflammation. These results indicate that the pharmaceutical composition or alkaloid composition can effectively inhibit the inflammation occurred in respiratory tract, and have the effect of treating a disease associated with over-expression of inflammation. Preferably, the pharmaceutical composition or alkaloid composition of the invention can be used to treat airway inflammation.

In the invention, in vivo pharmacodynamic studies on the pharmaceutical composition or alkaloid composition were conducted. The results showed: after intragastrical administration for 7 days continuously, the pharmaceutical composition or alkaloid composition significantly inhibit aggregation of inflammatory cell in chronic obstructive pulmonary disease duplicated by lipopolysaccharide plus smoke exposure, decrease the level of IL-6, CRP, enhance the activity of SOD, decrease the content of MDA, alleviate airway remodeling and airway obstruction, and improve symptom of airway obstruction. These results indicate that the pharmaceutical composition or alkaloid composition can effectively inhibit obstruction occurred in respiratory tract disease, and have the effect of treating a disease associated with airway obstruction and airflow limitation. Preferably, the pharmaceutical composition or alkaloid composition of the invention can be used to treat chronic obstructive pulmonary disease.

In some embodiments of the invention, the pharmaceutical composition or alkaloid composition of the invention can decrease Eotaxin and IgE in serum, significantly inhibit over-activation of alveolar eosinophil, reduce chemotaxis, infiltration and release of eosinophil, reduce the production of antibodies, and alleviate symptom of asthma.

In some embodiments of the invention, the pharmaceutical composition or alkaloid composition of the invention can decrease the level of IL-4 in lavage fluid, increase the content of IL-10, reduce the production of antibodies, and alleviate symptom of asthma.

In the invention, in vivo pharmacodynamic studies on the pharmaceutical composition or alkaloid composition were conducted. The results showed: after intragastrical administration for 7 days continuously, the pharmaceutical composition or alkaloid composition could significantly inhibit aggregation of inflammatory cell in asthma disease duplicated by ovalbumin, reduce Eotaxin, IgE and IL-4, increase the content of IL-10, and improve symptom of asthma. These results indicate that the pharmaceutical composition or alkaloid composition can effectively inhibit the release of proinflammatory factor, increase the content of anti-inflammatory factor, inhibit the production of immunoglobulin IgE, and have the effect of treating a disease associated with allergy. Preferably, the pharmaceutical composition or alkaloid composition of the invention can be used to treat asthma.

In some embodiments of the invention, the pharmaceutical composition or alkaloid composition of the invention can decrease the level of KL-6 and LDH in serum, alleviate the injury of alveolar epithelial cell and the injured degree of lung tissue blood-air barrier function, and have a preventive and therapeutic effect on pulmonary fibrosis.

In some embodiments of the invention, the pharmaceutical composition or alkaloid composition of the invention can decrease the level of TGF-β, Col-1, Hyp in tissue, reduce the formation of pulmonary collagen fiber, and have a preventive and therapeutic effect on pulmonary fibrosis.

In the invention, in vivo pharmacodynamic studies on the pharmaceutical composition or alkaloid composition were conducted. The results showed: after intragastrical administration for 28 days continuously, the pharmaceutical composition could significantly inhibit the production of krebs von den lungen (涎液化糖链蛋白) in fibrosis disease duplicated by bleomycin, alleviate the injury of alveolar epithelial cell, inhibit fibrosis, and therefore have a protective effect on pulmonary fibrosis. These results indicate that the pharmaceutical composition or alkaloid composition can effectively alleviate the injury of alveolar epithelial cell, reduce the formation of extracellular matrix, decrease the content of hydroxyproline, reduce the formation of collagen fiber, and have the effect of treating a disease associated with fibrosis. Preferably, the pharmaceutical composition or alkaloid composition of the invention can be used to treat pulmonary fibrosis.

Beneficial Effects of the Invention

The invention provides an alkaloid composition extracted from leaves of *Alstonia scholaris*. The invention further provides a pharmaceutical composition, comprising one or more of picrinine, vallesamine, scholaricine and 19-epischolaricine. The alkaloid composition extracted from leaves of *Alstonia scholaris* or the pharmaceutical composition has a significant therapeutic effect on respiratory disease. The pharmaceutical composition or alkaloid composition can achieve at least one of the following technical effects:

(1) the pharmaceutical composition or alkaloid composition of the invention can decrease the level of IL-8 in lung tissue and serum, reduce the production of IL-8, reduce neutrophil chemotaxis, and alleviate the injury to airway and lung tissue; can inhibit over-activation of alveolar macrophages, reduce chemotaxis, infiltration and release of inflammatory cell, and reduce hyperreactivity of airway, by decreasing the content of TNF-α; increasing the content of NO in serum, lung tissue, and lavage fluid, improve the oxidation-antioxidation balance in organism, and lower the injured degree of cell in organism; prevent aggregation of inflammatory cell, alleviate airway inflammation, and be used to treat airway inflammation caused by infection factor;

(2) the pharmaceutical composition or alkaloid composition of the invention can decrease the level of IL-6 and CRP in serum, enhance antioxidant activity in organism, reduce infiltration of leukocyte and neutrophil, and can be used to treat chronic obstructive pulmonary disease;

(3) The pharmaceutical composition or alkaloid composition of the invention can decrease the level of Eotaxin, IgE in serum and the content of IL-4 in bronchoalveolar lavage fluid, increase the content of IL-10 in bronchoalveolar lavage fluid, improve the oxidation-antioxidation balance in organism, reduce infiltration of leukocyte and eosinophil, and can be used to treat asthma; and (4) The pharmaceutical composition or alkaloid composition of the invention can decrease the level of KL-6, LDH in serum, and the content of TGF-β, Col-1, HYP and MMP-1 in homogenate, improves the oxidation-antioxidation balance in organism, and can be used to treat pulmonary fibrosis disease.

DESCRIPTION OF THE DRAWINGS

FIG. 1 shows the effect of the pharmaceutical composition and alkaloid composition of the invention on pathologic state of lung tissue in LPS-induced rat.

DETAILED DESCRIPTION OF THE INVENTION

Specific Modes for Carrying Out the Invention

The embodiments of the invention are described by combining the following examples. However, a person skilled in the art understands that the following examples are only intended to describe the invention, and shall not be regarded as defining the scope of the invention. In the case where the concrete conditions are not indicated in the examples, the examples are carried out according to conventional conditions or the conditions recommended by the manufacturer. The reagents or apparatuses, the manufacturers of which are not indicated, are the conventional products that are commercially available.

Example 1 Preparation of an Alkaloid Composition and a Pharmaceutical Composition Example 1.1 Preparation of an Alkaloid Composition Leaves of *Alstonia scholaris* (10 kg) were subjected to reflux extraction with 150 L 70% ethanol twice, and concentrated under reduced pressure to obtain a concrete. The concrete was soaked with 15 L 0.5% hydrochloric acid for three times, and the obtained acidic aqueous solution was concentrated and dried to obtain an acidic ethanol extract (1.2 kg); the obtained acidic ethanol extract (1.2 kg) was dissolved in 15 L water, and then 20% ammonia water solution was used to adjust pH to 10.5. The resultant solution was extracted with ethyl acetate for four times. The ethyl acetate phase was concentrated under reduced pressure, the solvent was recovered, and the residue was dried to obtain an alkaloid composition (90 g).

Example 1.2 Preparation of an Alkaloid Composition

Leaves of *Alstonia scholaris* (10 kg) were subjected to reflux extraction with 200 L 60% ethanol twice, and concentrated under reduced pressure to obtain a concrete. The concrete was soaked with 20 L 1% hydrochloric acid for three times, and the obtained acidic aqueous solution was concentrated and dried to obtain an acidic ethanol extract (1.2 kg). The obtained acidic ethanol extract (1.2 kg) is dissolved in 18 L water, and then 1% hydrochloric acid solution was used to adjust pH to 2.5. The acidic aqueous solution was loaded to LSD001 cation exchange resin, and eluted with water, followed by elution with ethanol-ammonia water (25%) at a ratio of 2:1. The eluent eluted by the ethanol-ammonia water was collected, and concentrated under reduced pressure, the solvent was recovered, and the residue was dried to obtain an alkaloid composition (135 g).

Example 1.3 Preparation of an Alkaloid Composition

Leaves of *Alstonia scholaris* (10 kg) were subjected to reflux extraction with 50 L 90% ethanol for three times, and concentrated under reduced pressure to obtain a concrete. The concrete was soaked with 5 L 0.05% sulfuric acid for five times, and the obtained acidic aqueous solution was concentrated and dried to obtain an acidic ethanol extract (1.3 kg). The obtained acidic ethanol extract (1.3 kg) was dissolved in 5 L water, and then 10% NaOH aqueous solution was used to adjust pH to 7.5. The resultant solution was extracted with ethyl acetate for four times. The ethyl acetate phase was concentrated under reduced pressure, the solvent was recovered, and the residue was dried to obtain an alkaloid composition (98 g).

Example 1.4 Preparation of an Alkaloid Composition

Leaves of *Alstonia scholaris* (10 kg) were subjected to reflux extraction with 100 L 75% ethanol for three times, and concentrated under reduced pressure to obtain a concrete. The concrete was soaked with 10 L 0.03% sulfuric acid for five times, and the obtained acidic aqueous solution was concentrated and dried to obtain an acidic ethanol extract (1.3 kg). The obtained acidic ethanol extract was dissolved in 10 L water, and then 0.1% $H_2SO_4$ aqueous solution was used to adjust pH to 5.5. The acidic aqueous solution was loaded to ion exchange resin 001×7, and eluted with water, followed by elusion with ethanol-ammonia water at a ratio of 3:1. The eluent eluted by the ethanol-ammonia water was collected, and concentrated under reduced pressure, the solvent was recovered, and the residue was dried to obtain an alkaloid composition (139 g).

Example 1.5 Preparation of an Alkaloid Composition

Leaves of *Alstonia scholaris* (10 kg) were subjected to reflux extraction with 100 L 80% ethanol for three times, and concentrated under reduced pressure to obtain a concrete. The concrete was soaked with 0.4% hydrochloric acid 10 L for three times, and the obtained acidic aqueous solution was concentrated and dried to obtain an acidic ethanol extract (1.35 kg). The obtained acidic ethanol extract was dissolved in 10 L water, and then 30% $Na_2CO_3$ aqueous solution was used to adjust pH to 8.5. The resultant solution was extracted with ethyl acetate for four times. The ethyl acetate phase was concentrated under reduced pressure, the solvent was recovered, and the residue was dried to obtain an alkaloid composition (91 g).

Example 1.6 Preparation of an Alkaloid Composition

Leaves of *Alstonia scholaris* (10 kg) were subjected to reflux extraction with 100 L 85% ethanol for three times, and concentrated under reduced pressure to obtain a concrete. The concrete was soaked with 0.3% hydrochloric acid 10 L for three times, and the obtained acidic aqueous solution was concentrated and dried to obtain an acidic ethanol extract (1.35 kg). The obtained acidic ethanol extract was dissolved in 15 L water, and then 5% HCl aqueous solution was used to adjust pH to 4.5. The acidic aqueous solution was loaded to ion exchange resin 001×4, and eluted with water, followed by elution with ethanol-ammonia water at a ratio of 4:1. The eluent eluted by the ethanol-ammonia water was collected, and concentrated under reduced pressure, the solvent was recovered, and the residue was dried to obtain an alkaloid composition (141 g).

Example 1.7 Preparation of Picrinine, Vallesamine, Scholaricine and 19-Epischolaricine from an Alkaloid Composition The total alkaloids obtained in any example of Examples 1.1-1.6 were mixed with twice the amount of silica gel, loaded to chromatographic column containing 10 times the amount of silica gel, and washed with $CHCl_3$-MeOH (30:1-1:1). By monitoring with TLC, using a standard as reference, and developing color with a chromogenic agent specific for alkaloids, i.e. bismuth potassium iodide, fractions comprising picrinine, vallesamine, scholaricine or 19-epischolaricine were collected, respectively, to obtain pure forms of picrinine, vallesamine, scholaricine, and 19-epischolaricine.

Example 1.8 Preparation of a Pharmaceutical Composition (1) Raw materials were weighed at the following ratio by weight: 8-50 parts by weight of picrinine, 5-45 parts by weight of vallesamine, 5-30 parts by weight of scholaricine, and 0-10 parts by weight of 19-epischolaricine obtained in Example 1.7; the alkaloid components were mixed at said different ratios, and volatile oil was added by spraying. The resultant mixture was directly packaged and sealed to obtain the composition.

Or, (2) to all the raw materials in a formulation, starch and dextrin were added, and the resultant mixture was prepared into a heterotypical tablet (异型片) in accordance with a conventional method, at 0.5 g per tablet.

Or, (3) The total alkaloids prepared in Examples 1.1-1.6 were mixed with at least one of picrinine, vallesamine, scholaricine or 19-epischolaricine prepared in Example 1.7, so that the composition comprised 8-50 parts by weight of picrinine, 5-45 parts by weight of vallesamine, 5-30 parts by weight of scholaricine, and 0-10 parts by weight of 19-epischolaricine. Starch and dextrin were then added, and the resultant mixture was compressed into tablets in accordance with a conventional method.

Example 2 Preparation of an Injection Formulation

To the pharmaceutical composition prepared in accordance with the method described in Example 1.8, water for injection was added conventionally. After refined filtration, encapsulation and sterillization, the injection was prepared.

Example 3 Preparation of a Powder-Injection

The pharmaceutical composition prepared in accordance with the method described in Example 1.8, was dissolved in sterile water for injection, under stirring, and was subjected to sterile suction filtration with a funnel, and then to sterile refined filtration. The filtrate was subpackaged into two ampules, and were subjected to sterile sealing to obtain a sterile powder for injection after low-temperature freeze-drying.

Example 4 Preparation of a Powder

To the pharmaceutical composition prepared in accordance with the method described in Example 1.8, an excipient was added at a ratio of 9:1 by weight, to prepare a powder.

Example 5 Preparation of a Tablet

To the pharmaceutical composition prepared in accordance with the method described in Example 1.8, an excipient was added a ratio of 1:5-1:10 by weight, and the mixture was granulated and compressed to prepare a tablet.

Example 6 Preparation of an Oral Liquid Formulation

The pharmaceutical composition prepared in accordance with the method described in Example 1.8, was subjected to a conventional method for preparing oral liquids to prepare an oral liquid.

Example 7 Preparation of a Capsule, a Granule or an Electuary

To the pharmaceutical composition prepared in accordance with the method described in Example 1.8, an excipient was added at a ratio of 5:1 by weight, to prepare a capsule, a granule or an electuary.

Example 8 Preparation of a Capsule, a Granule or an Electuary

To the pharmaceutical composition prepared in accordance with the method described in Example 1.8, an excipient was added at a ratio of 3:1 by weight, to prepare a capsule, a granule or an electuary.

Example 9: The Therapeutic Effect of the Pharmaceutical Composition and Alkaloid Composition of the Invention on Airway Inflammation Animal source: 190~220 g male SD rat, from laboratory animal department of Kunming Medical University, License No. SCXK (Dian) 2011-0004.

Method and route: lipopolysaccharide (LPS) was used to induce a rat airway inflammation model; after intragastrical administration for 7 d at a dose of 10 mL/kg, the animal was sacrificed at the eighth day.

Group and dose: Sham operation group (Sham), Model group (LPS), positive control dexamethasone (DXM) Group at 1.5 mg/kg, Test group 1: picrinine, vallesamine, scholaricine and 19-epischolaricine prepared in Example 1.7 were homogeneously mixed at different ratios by weight (30 mg/kg), Test group 2: picrinine, vallesamine, scholaricine and 19-epischolaricine prepared in Example 1.7 were homogeneously mixed (15 mg/kg), and Test group 3: the alkaloid composition prepared in Example 1.1 (7.5 mg/kg).

Positive control: dexamethasone tablet, Approval number: H12020686, 0.75 mg/tablet, produced by Tianjin Tianyao Pharmaceuticals Co., Ltd., Batch No. 100102.

Sample preparation: all the samples were prepared by using 0.5% carboxymethylcellulose sodium (0.5% CMC-Na).

(1) Effect on Inflammatory Cell and Classification Thereof in Lipopolysaccharide-Induced Rat:

Group and dose: in Test group 1 and Test group 2, the ratio of picrinine, vallesamine, scholaricine and 19-epischolaricine by weight was 43:16:30:8 and 20:38:30:7, respectively, and the other groups and doses thereof were as described in Example 9.

Test index: Total number of white blood cells (WBCs) and inflammatory cell classification in bronchoalveolar lavage fluid (BALF) were used as indexes. The result was shown in Table 1.

cine by weight was 48:10:30:9 and 12:14:15:6, respectively, and the other groups and doses thereof were as described in Example 9.

Test index: IL-8 in bronchoalveolar lavage fluid (BALF), serum, and homogenate was used as index. The result was shown in Table 2.

TABLE 2

Effect on IL-8 in LPS-induced rat

| Group | dose (/kg) | IL-8 ($\bar{x} \pm S$, pg/mL) | | |
|---|---|---|---|---|
| | | serum | BALF | lung tissue |
| Sham | — | 25.52 ± 8.97 | 15.57 ± 5.01 | 46.92 ± 26.01 |
| LPS | 10 ml | 48.42 ± 21.93$^\Delta$ | 56.62 ± 24.63$^{\Delta\Delta}$ | 97.02 ± 27.32$^{\Delta\Delta}$ |
| DXM | 1.5 mg | 29.62 ± 12.13* | 24.62 ± 12.42** | 60.62 ± 20.11** |
| Test group 1 | 30 mg | 33.22 ± 18.55 | 36.22 ± 15.36* | 64.22 ± 19.62** |
| Test group 2 | 15 mg | 31.72 ± 13.09 | 31.72 ± 15.58* | 70.72 ± 26.87* |
| Test group 3 | 7.5 mg | 29.22 ± 13.08* | 30.22 ± 14.57* | 65.22 ± 18.71** |

As compared to Sham group, $^{\Delta/\Delta\Delta}p < 0.05/0.01$; as compared to LPS group, */**$P < 0.05/0.01$;

The experimental result showed: both the pharmaceutical composition and alkaloid composition of the invention could significantly decrease the level of IL-8 in BALF and lung tissue; the alkaloid composition could significantly decrease the level of IL-8 in serum; and therefore, the

TABLE 1

Effect on inflammatory cell in LPS-induced rat ($\bar{x} \pm S$)

| Group | dose (/kg) | WBC (× 10$^5$/ml) | BALF cell classification* (%) | | | |
|---|---|---|---|---|---|---|
| | | | AM | N | L | M |
| Sham | — | 1.52 ± 0.68 | 67.0 ± 8.4 | 7.6 ± 2.4 | 13.1 ± 3.3 | 12.4 ± 3.4 |
| LPS | 10 ml | 7.05 ± 2.29$^{\Delta\Delta}$ | 40.5 ± 7.4$^{\Delta\Delta}$ | 43.9 ± 6.3$^{\Delta\Delta}$ | 7.8 ± 2.5$^{\Delta\Delta}$ | 7.8 ± 2.6$^{\Delta\Delta}$ |
| DXM | 1.5 mg | 3.35 ± 1.89** | 52.5 ± 7.0** | 8.2 ± 2.9** | 9.3 ± 5.0 | 28.9 ± 6.20** |
| Test group 1 | 30 mg | 4.00 ± 2.43** | 52.5 ± 14.6* | 17.2 ± 7.6** | 10.2 ± 3.9 | 19.3 ± 7.4** |
| Test group 2 | 15 mg | 4.79 ± 2.51* | 48.8 ± 9.7* | 16.5 ± 3.9** | 9.6 ± 3.7 | 25.2 ± 8.5** |
| Test group 3 | 7.5 mg | 3.71 ± 1.64** | 49.9 ± 7.5* | 16.9 ± 5.5** | 9.4 ± 2.1 | 22.8 ± 6.1** |

As compared to Sham group, $^{\Delta\Delta}P < 0.01$;
as compared to LPS group, */**$P < 0.05/0.01$;
*AM: alveolar macrophage;
N: neutrophil;
L: lymphocyte;
M: monocyte The experimental results showed: both the pharmaceutical composition and alkaloid composition of the invention could significantly lower the total number of white blood cells (WBCs) and the percentage of neutrophils (N %) in BALF of model rat, and significantly increase the percentage of macrophages (AM %) and monocytes (M %), and had statistical difference as compared to control group (P<0.05/0.01); thereby indicating that the pharmaceutical composition and alkaloid composition could effectively prevent aggregation of inflammatory cell, and significantly alleviate airway inflammation.

(2) Effect on Interleukin-8 (IL-8) in Lipopolysaccharide-Induced Rat:

Group and dose: in Test group 1 and Test group 2, the ratio of picrinine, vallesamine, scholaricine and 19-epischolaripharmaceutical composition and alkaloid composition of the invention could reduce the production of IL-8, reduce neutrophil chemotaxis, and alleviate the injury to airway and lung tissue.

(3) Effect on Tumor Necrosis Factor-α (TNF-α) in Lipopolysaccharide-Induced Rat:

Group and dose: in Test group 1 and Test group 2, the ratio of picrinine, vallesamine, scholaricine and 19-epischolaricine by weight was, 45:36:7:10 and 10:18:9:2, respectively, and the other groups and doses thereof were as described in Example 9.

Test index: TNF-α in bronchoalveolar lavage fluid (BALF), serum, and homogenate was used as index. The result was shown in Table 3.

TABLE 3

Effect on TNF-α in LPS-induced rat

| Group | dose (/kg) | TNF-a ($\bar{x} \pm S$, pg/mL) | | |
|---|---|---|---|---|
| | | Serum | BALF | lung tissue |
| Sham | — | 5.21 ± 1.68 | 7.64 ± 2.02 | 15.22 ± 1.68 |
| LPS | 10 ml | 6.98 ± 1.76$^\Delta$ | 19.73 ± 6.42$^{\Delta\Delta}$ | 235.98 ± 53.47$^{\Delta\Delta}$ |
| DXM | 1.5 mg | 5.11 ± 1.67* | 11.28 ± 4.51** | 152.11 ± 37.64** |
| Test group 1 | 30 mg | 6.01 ± 1.64 | 13.00 ± 5.28* | 175.01 ± 32.67** |
| Test group 2 | 15 mg | 5.81 ± 1.34 | 13.43 ± 6.46* | 183.81 ± 34.09* |
| Test group 3 | 7.5 mg | 6.31 ± 1.66 | 12.43 ± 4.41** | 169.31 ± 33.66** |

As compared to Sham group, $^{\Delta/\Delta\Delta}p < 0.05/0.01$; as compared to LPS group, */**P < 0.05/0.01;

The experimental result showed: after the treatment with the pharmaceutical composition and alkaloid composition of the invention, the level of TNF-α in rat lung tissue and bronchoalveolar lavage fluid was significantly decreased, indicating that the pharmaceutical composition and alkaloid composition of the invention could inhibit over-activation of alveolar macrophages, reduce chemotaxis, infiltration and release of inflammatory cell, and reduce hyperreactivity of airway, by decreasing the content of TNF-α.

(4) Effect on Nitrogen Monoxide (NO) in Lipopolysaccharide-Induced Rat:

Group and dose: in Test group 1 and Test group 2, the ratio of picrinine, vallesamine, scholaricine and 19-epischolaricine by weight was 40:30:28:2 and 15:18:26:7, respectively, and the other groups and doses thereof were as described in Example 9.

Test index: NO in bronchoalveolar lavage fluid (BALF), serum, and homogenate was used as index. The result was shown in Table 4.

TABLE 4

Effect on NO in LPS-induced rat

| Group | Dose (/kg) | NO ($\bar{x} \pm S$, umol/L) | | |
|---|---|---|---|---|
| | | Serum | BALF | Lung tissue |
| Sham | — | 31.81 ± 11.73 | 16.31 ± 3.17 | 23.47 ± 8.62 |
| LPS | 10 ml | 17.78 ± 9.44$^{\Delta\Delta}$ | 9.97 ± 3.75$^{\Delta\Delta}$ | 11.71 ± 5.94$^{\Delta\Delta}$ |
| DXM | 1.5 mg | 27.20 ± 7.67* | 13.52 ± 4.17 | 18.35 ± 5.30* |
| Test group 1 | 30 mg | 26.21 ± 7.82* | 12.78 ± 3.23 | 19.24 ± 6.62* |
| Test group 2 | 15 mg | 29.39 ± 11.02* | 11.31 ± 4.37 | 17.59 ± 5.93* |
| Test group 3 | 7.5 mg | 28.86 ± 10.33* | 12.30 ± 3.27 | 21.47 ± 9.64* |

As compared to Sham group, $^{\Delta/\Delta\Delta}p < 0.05/0.01$; as compared to LPS group, *P < 0.05;

The experimental result showed: in tracheitis induced by LPS, airway and pulmonary epithelium, endothelial cell and alveolar macrophage, etc. had a reduced ability of synthesizing and releasing NO. After the treatment with the pharmaceutical composition and alkaloid composition of the invention, the content of NO in serum and lung tissue was significantly increased, and the content of NO in lavage fluid had a tendency of increase, and the disturbance in oxidation-antioxidation balance in organism was improved, so as to alleviate the injured degree of cells in organism.

(5) Effect on Superoxide Dismutase (SOD) in Lipopolysaccharide-Induced Rat:

Group and dose: in Test group 1 and Test group 2, the ratio of picrinine, vallesamine, scholaricine and 19-epischolaricine by weight was 8:45:29:9 and 20:14:12:7, respectively, and the other groups and doses thereof were as described in Example 9.

Test index: SOD in bronchoalveolar lavage fluid (BALF), serum, and homogenate was used as index. The result was shown in Table 5.

TABLE 5

Effect on SOD in LPS-induced rat

| Group | dose (/kg) | SOD ($\bar{x} \pm S$, U/mL) | | |
|---|---|---|---|---|
| | | Serum | BALF | Lung tissue |
| Sham | — | 381.5 ± 114.6 | 63.27 ± 8.08 | 100.82 ± 10.09 |
| LPS | 10 ml | 206.7 ± 87.0$^{\Delta\Delta}$ | 44.44 ± 15.37$^{\Delta\Delta}$ | 72.46 ± 5.22$^{\Delta\Delta}$ |
| DXM | 1.5 mg | 307.6 ± 97.7* | 63.35 ± 13.45* | 92.25 ± 8.88** |
| Test group 1 | 30 mg | 301.2 ± 106.0* | 58.14 ± 11.34* | 85.26 ± 11.42** |
| Test group 2 | 15 mg | 256.7 ± 93.0 | 56.53 ± 12.24 | 81.27 ± 8.84* |
| Test group 3 | 7.5 mg | 291.2 ± 89.2* | 63.02 ± 10.84** | 90.33 ± 8.81** |

As compared to Sham group, $^{\Delta/\Delta\Delta}p < 0.05/0.01$; as compared to LPS group, */** P <0.05/0.01;

The experimental result showed: after the treatment, the pharmaceutical composition and alkaloid composition of the invention could enhance the activity of SOD in serum, bronchoalveolar lavage fluid and lung tissue to different extents. The pharmaceutical composition and alkaloid composition of the invention could clean the injury of free radical to organism, and have a certain effect on maintaining the balance of free radical generation and clearance.

(6) Effect on Lipid Peroxidation Product (MDA) in Lipopolysaccharide-Induced Rat:

Group and dose: in Test group 1 and Test group 2, the ratio of picrinine, vallesamine, scholaricine and 19-epischolaricine by weight was 45:6:28:3 and 17:14:9:4, respectively, and the other groups and doses thereof were as described in Example 9.

Test index: MDA in bronchoalveolar lavage fluid (BALF), serum, and homogenate was used as index. The result was shown in Table 6.

TABLE 6

Effect on MDA in LPS-induced rat

| Group | dose (/kg) | MDA ($\bar{x} \pm S$, nmol/mL) | | |
|---|---|---|---|---|
| | | Serum | BALF | lung tissue |
| Sham | — | 3.31 ± 1.43 | 4.11 ± 1.49 | 1.11 ± 0.69 |
| LPS | 10 ml | 5.98 ± 1.43$^{\Delta\Delta}$ | 6.78 ± 1.66$^{\Delta\Delta}$ | 2.98 ± 1.17$^{\Delta\Delta}$ |
| DXM | 1.5 mg | 4.21 ± 1.49* | 4.81 ± 1.30** | 1.61 ± 0.71** |
| Test group 1 | 30 mg | 4.21 ± 1.48* | 4.91 ± 1.34* | 2.03 ± 0.46* |
| Test group 2 | 15 mg | 4.91 ± 1.71 | 5.39 ± 1.66 | 2.11 ± 0.40* |
| Test group 3 | 7.5 mg | 4.51 ± 1.66* | 4.86 ± 1.58** | 1.91 ± 0.69* |

As compared to Sham group, $^{\Delta\Delta}P < 0.01$; as compared to LPS group, */**$P < 0.05/0.01$;

The experimental result showed: during the development of airway inflammation, a lot of lipid peroxidation products aggregated, and after the treatment of the groups, the content of MDA in lung tissue was decreased significantly; and the content of MDA in serum and BALF had a tendency of decrease. Therefore, the pharmaceutical composition and alkaloid composition of the invention could significantly improve the disturbance in oxidization-antioxidization balance in vivo, and therefore could alleviate the injured degree of cells in organism.

(7) Effect on Albumin (ALB) in Lipopolysaccharide-Induced Rat:

Group and dose: in Test group 1 and Test group 2, the ratio of picrinine, vallesamine, scholaricine and 19-epischolaricine by weight was 36:38:7:1 and 16:15:14:5, respectively, and the other groups and doses thereof were as described in Example 9.

Test index: ALB in bronchoalveolar lavage fluid (BALF), and serum was used as index. The result was shown in Table 7.

TABLE 7

Effect on ALB in LPS-induced rat

| Group | dose (/kg) | ALB (g/L) | |
|---|---|---|---|
| | | BALF | Serum |
| Sham | — | 0.02 ± 0.05 | 18.4 ± 1.6 |
| LPS | 10 ml | 0.33 ± 0.13$^{\Delta\Delta}$ | 16.3 ± 1.1$^{\Delta\Delta}$ |
| DXM | 1.5 mg | 0.18 ± 0.07** | 19.4 ± 1.4** |
| Test group 1 | 30 mg | 0.22 ± 0.06* | 17.4 ± 1.2* |
| Test group 2 | 15 mg | 0.22 ± 0.09* | 17.9 ± 2.0* |
| Test group 3 | 7.5 mg | 0.19 ± 0.09* | 17.7 ± 1.4* |

As compared to Sham group, $^{\Delta\Delta}P < 0.01$; as compared to LPS group, *$P < 0.05$;

The experimental result showed: during the development of airway inflammation, the pulmonary alveolar epithelial-capillary barrier was injured, so that the ALB in blood could pass through the barrier, resulting in an increase in ALB in bronchoalveolar lavage fluid, and a decrease in ALB in serum. After the treatment with the pharmaceutical composition and alkaloid composition of the invention, ALB in both bronchoalveolar lavage fluid and lung tissue was significantly improved. The pharmaceutical composition and alkaloid composition of the invention could repair the injured pulmonary alveolar epithelial-capillary barrier.

(8) Effect on Alkaline Phosphatase (AKP) in Lipopolysaccharide-Induced Rat:

Group and dose: in Test group 1 and Test group 2, the ratio of picrinine, vallesamine, scholaricine and 19-epischolaricine by weight was 8:25:30:9 and 12:10:9:2, respectively, and the other groups and doses thereof were as described in Example 9.

Test index: AKP in bronchoalveolar lavage fluid (BALF), and serum was used as index. The result was shown in Table 8.

TABLE 8

Effect on AKP in LPS-induced rat

| Group | dose (/kg) | AKP (U/L) | |
|---|---|---|---|
| | | BALF | Serum |
| Sham | — | 33.4 ± 12.3 | 296.6 ± 114.4 |
| LPS | 10 ml | 59.5 ± 32.2$^{\Delta}$ | 271.1 ± 137.8 |
| DXM | 1.5 mg | 29.0 ± 5.9** | 116.1 ± 36.0** |
| Test group 1 | 30 mg | 26.2 ± 7.9** | 197.4 ± 58.8 |
| Test group 2 | 15 mg | 25.2 ± 20.8* | 214.3 ± 56.4 |
| Test group 3 | 7.5 mg | 24.7 ± 9.9** | 264.7 ± 114.3 |

As compared to Sham group, $^{\Delta}P < 0.05/0.01$; as compared to LPS group, */**$P < 0.05/0.01$;

The experimental result showed: during the development of airway inflammation, alveolar type II epithelial cell and other cells were injured. After the treatment of the groups, ALB in bronchoalveolar lavage fluid was significantly improved. It indicated that both the pharmaceutical composition and alkaloid composition of the invention could repair the injured alveolar type II epithelial cell and other cells.

(9) Effect on Lactate Dehydrogenase (LDH) in Lipopolysaccharide-Induced Rat:

Group and dose: in Test group 1 and Test group 2, the ratio of picrinine, vallesamine, scholaricine and 19-epischolaricine by weight was 10:28:15:8 and 10:7:7:2, respectively, and the other groups and doses thereof were as described in Example 9.

Test index: LDH in bronchoalveolar lavage fluid (BALF), and serum was used as index. The result was shown in Table 9.

TABLE 9

Effect on LDH in LPS-induced rat

| Group | dose (/kg) | LDH (U/L) | |
|---|---|---|---|
| | | BALF | Serum |
| Sham | — | 219.4 ± 86.7 | 404.0 ± 128.4 |
| LPS | 10 ml | 355.0 ± 178.9$^{\Delta}$ | 894.7 ± 429.5$^{\Delta\Delta}$ |
| DXM | 1.5 mg | 96.7 ± 25.6** | 386.5 ± 92.7** |
| Test group 1 | 30 mg | 193.3 ± 107.1* | 567.5 ± 187.3* |
| Test group 2 | 15 mg | 160.9 ± 101.8** | 536.8 ± 232.5* |
| Test group 3 | 7.5 mg | 257.4 ± 107.1* | 494.9 ± 136.0* |

As compared to Sham group, $^{\Delta/\Delta\Delta}P < 0.05/0.01$; as compared to LPS group, */**$P < 0.05/0.01$;

The experimental result showed: during the development of airway inflammation, cells were injured, cell membrane permeability increased or cell died, and in all these cases, LDH could be released to the outside of cell. After the treatment of the groups, LDH in bronchoalveolar lavage fluid and serum was significantly improved, and both the pharmaceutical composition and alkaloid composition of the invention could alleviate the injured degree of cells.

(10) Effect on Pathogenic State of Lung Tissue in Lipopolysaccharide-Induced Rat:

Group and dose: in Test group 1 and Test group 2, the ratio of picrinine, vallesamine, scholaricine and 19-epischolaricine by weight was 8:41:27:1 and 8:5:5:1, respectively, and the other groups and doses thereof were as described in Example 9.

Test index: LDH in bronchoalveolar lavage fluid (BALF), and serum was used as index. The result was shown in FIG. 1.

The experimental result showed: during the development of airway inflammation, consolidation of lung tissue occurred, alveolar cavity narrowed significantly, alveolar wall thickened significantly, and interstitium was filled with a lot of cells, accompanied by hyperplasia of a few fibrous connective tissues, or not. After the treatment of the groups, the number of diseased animals and the pathogenic degree were significantly lowered, indicating that both the pharmaceutical composition and the alkaloid composition of the invention could resist histomorphological changes of airway inflammation.

Example 10: Therapeutic Effect of the Pharmaceutical Composition and Alkaloid Composition of the Invention on Chronic Obstructive Pulmonary Disease (COPD)

Animal source: 25~30 g male ICR mouse, from laboratory animal department of Kunming Medical University, License No. SCXK (Dian) 2011-0004.

Method and route: lipopolysaccharide (LPS) plus smoke exposure was used for 30 days to induce mouse chronic obstructive pulmonary disease model; and after intragastrical administration for 7 d at a dose of 20 mL/kg, the animal was sacrificed at the eighth day.

Group and dose: Sham group, Model group, Positive control group, dexamethasone (2 mg/kg), Test group 1: picrinine, vallesamine, scholaricine and 19-epischolaricine prepared in Example 1.7 were mixed at different ratios by weight (50 mg/kg), Test group 2: the alkaloid composition (25 mg/kg) prepared in Example 1.2, Test group 3: the alkaloid composition (10 mg/kg) prepared in Example 1.3. Picrinine group (10 mg/kg), Vallesamine group (6.0 mg/kg), Scholaricine group (7.0 mg/kg), 19-epischolaricine group (2.0 mg/kg).

Dexamethasone acetate tablet, Approval number: H33020822, 0.75 mg/tablet, produced by Zhejiang Xianju Pharmaceutical Co., Ltd., Batch No. 140329.

Sample preparation: all the samples were prepared by using 0.5% carboxymethylcellulose sodium (0.5% CMC-Na).

(1) Effect on Inflammatory Cell and Classification Thereof in Lipopolysaccharide Plus Smoke Exposure-Induced COPD Mouse:

Group and dose: in Test group 1, the ratio of picrinine, vallesamine, scholaricine and 19-epischolaricine by weight was 48:40:29:10, and the other groups and doses thereof were as described in Example 10.

Test index: total number of white blood cells and inflammatory cell classification in bronchoalveolar lavage fluid (BALF) were used as indexes, and were determined by full-automatic hemocytometer. The result was shown in Table 10.

The experimental result showed: the pharmaceutical composition, alkaloid composition and four monomeric compounds of the invention could significantly lower the total number of white blood cells (WBCs) and the neutrophil percentage (N %) in BALF of model rat, wherein the three test groups of the pharmaceutical composition and alkaloid composition, the picrinine group and the 19-epi-scholaricine group had a statistic difference as compared to Control group (P<0.01); thereby indicating that the pharmaceutical composition and alkaloid composition, picrinine and 19-epi-scholaricine could effectively prevent the aggregation of inflammatory cell in COPD model.

(2) Effect on Interleukin-6 (IL-6) in Serum of Lipopolysaccharide Plus Smoke Exposure-Induced COPD Model Mouse:

Group and dose: in Test group 1, the ratio of picrinine, vallesamine, scholaricine and 19-epischolaricine by weight was 38:30:27:7, and the other groups and doses thereof were as described in Example 10.

Test index: IL-6 in serum was used as index, and was determined by enzyme linked immunosorbent assay. The result was shown in Table 11.

TABLE 11

Effect on IL-6 in serum of COPD model mouse ($\bar{x} \pm SD$, pg/mL)

| Group | Dose (/kg) | Animal (number) | Administration Route | IL-6 |
|---|---|---|---|---|
| Sham | — | 9 | ig | 20.8 ± 2.2 |
| Model | 10 mL | 10 | ig | 26.5 ± 3.4$^\Delta$ |
| dexamethasone | 1 mg | 10 | ig | 22.0 ± 2.0* |
| Test group 1 | 50 mg | 10 | ig | 23.2 ± 4.2 |
| Test group 2 | 25 mg | 10 | ig | 24.1 ± 2.4 |
| Test group 3 | 10 mg | 10 | ig | 22.7 ± 2.0* |
| picrinine | 10 mg | 10 | ig | 23.9 ± 3.9 |
| vallesamine | 6 mg | 10 | ig | 25.0 ± 3.6 |
| scholaricine | 7 mg | 10 | ig | 22.2 ± 3.0* |
| 19-epi-scholaricine | 2 mg | 10 | ig | 23.3 ± 4.1 |

As compared to Sham group, $^\Delta$P < 0.05; as compared to Model group, *P < 0.05;

The experimental result showed: both the pharmaceutical composition and scholaricine of the invention could significantly decrease the level of IL-6 in serum (p<0.05), and therefore, both the pharmaceutical composition and scholaricine of the invention could reduce the production of IL-6, reduce chemotaxis of inflammatory cell, and thus alleviate the injury to respiratory tract.

TABLE 10

Effect on white blood cell count and classification in BALF of COPD model mouse ($\bar{x} \pm SD$, ×10$^5$/mL)

| Group | dose (/kg) | Animal (number) | Administration route | Leukocyte number | Neutrophil number |
|---|---|---|---|---|---|
| Sham | — | 9 | ig | 1.1 ± 1.5 | 0.54 ± 0.38 |
| Model | 10 mL | 10 | ig | 3.8 ± 2.4$^\Delta$ | 1.1 ± 0.25$^\Delta$ |
| dexamethasone | 1 mg | 10 | ig | 1.1 ± 0.5* | 0.53 ± 0.50* |
| Test group 1 | 50 mg | 10 | ig | 1.5 ± 1.3 | 0.43 ± 0.26** |
| Test group 2 | 25 mg | 10 | ig | 1.6 ± 1.3 | 0.54 ± 0.26** |
| Test group 3 | 10 mg | 10 | ig | 1.1 ± 0.8* | 0.43 ± 0.25** |
| picrinine | 10 mg | 10 | ig | 2.1 ± 1.8 | 0.51 ± 0.29** |
| vallesamine | 6 mg | 10 | ig | 1.8 ± 1.7 | 0.75 ± 0.51 |
| scholaricine | 7 mg | 10 | ig | 2.5 ± 3.5 | 0.66 ± 0.81 |
| 19-epi-scholaricine | 2 mg | 10 | ig | 2.0 ± 1.6 | 0.62 ± 0.42* |

As compared to Sham group, $^\Delta$P < 0.05; as compared to Model group, */**P < 0.05/0.01;

(3) Effect on C-Reactive Protein (CRP) in Serum of Lipopolysaccharide Plus Smoke Exposure-Induced COPD Model Mouse:

Group and dose: in Test group 1, the ratio of picrinine, vallesamine, scholaricine and 19-epischolaricine by weight was 25:19:20:4, and the other groups and doses thereof were as described in Example 10.

Test index: CRP in serum was used as index, and was determined by enzyme linked immunosorbent assay. The result was shown in Table 12.

TABLE 12

Effect on CRP in serum in COPD model mouse
($\bar{x} \pm SD$, pg/mL)

| Group | Dose (/kg) | Animal (number) | Administration route | CRP |
|---|---|---|---|---|
| Sham group | — | 9 | ig | 20.8 ± 2.7 |
| Model | 10 mL | 10 | ig | 24.8 ± 1.7$^\Delta$ |
| dexamethasone | 1 mg | 10 | ig | 22.3 ± 2.0* |
| Test group 1 | 50 mg | 10 | ig | 22.7 ± 1.5* |
| Test group 2 | 25 mg | 10 | ig | 23.5 ± 2.0 |
| Test group 3 | 10 mg | 10 | ig | 22.9 ± 1.3* |
| picrinine | 10 mg | 10 | ig | 23.5 ± 2.2 |
| vallesamine | 6 mg | 10 | ig | 23.8 ± 1.9 |
| scholaricine | 7 mg | 10 | ig | 24.4 ± 2.4 |
| 19-epi-scholaricine | 2 mg | 10 | ig | 22.6 ± 1.8* |

As compared to Sham group, $^\Delta P < 0.05$; as compared to Model group, *P < 0.05;

The experimental result showed: the pharmaceutical composition, the alkaloid composition and 19-epi-scholaricine of the invention could significantly decrease the level of CRP in serum (p<0.05), and therefore, both the pharmaceutical composition, alkaloid composition of the invention and 19-epi-scholaricine could reduce the production of CRP, reduce the chemotaxis of inflammatory cell, and therefore alleviate injury to respiratory tract.

(4) Effect on Superoxide Dismutase (SOD) in Serum and Lung Homogenate of Lipopolysaccharide Plus Smoke Exposure-Induced COPD Model Mouse:

Group and dose: in Test group 1, the ratio of picrinine, vallesamine, scholaricine and 19-epischolaricine by weight was 16:11:12:3, and the other groups and doses thereof were as described in Example 10.

Test index: SOD in serum and lung homogenate was used as index, and was determined by xanthine oxidase method. The result was shown in Table 13.

TABLE 13

Effect on SOD in serum and homogenate of COPD model mouse ($\bar{x} \pm SD$, U/mL)

| Group | dose (/kg) | Animal (number) | Administration route | Serum | homogenate |
|---|---|---|---|---|---|
| Sham | — | 9 | ig | 93.48 ± 5.42 | 61.31 ± 3.61 |
| Model | 10 mL | 10 | ig | 85.51 ± 7.70$^\Delta$ | 53.37 ± 6.76$^\Delta$ |
| dexamethasone | 1 mg | 10 | ig | 86.85 ± 9.48 | 63.92 ± 5.84* |
| Test group 1 | 50 mg | 10 | ig | 92.15 ± 8.53 | 54.00 ± 16.65 |
| Test group 2 | 25 mg | 10 | ig | 97.70 ± 7.94* | 64.18 ± 4.61** |
| Test group 3 | 10 mg | 10 | ig | 94.71 ± 6.97* | 63.13 ± 6.89* |
| picrinine | 10 mg | 10 | ig | 91.15 ± 10.90 | 56.01 ± 12.78 |
| vallesamine | 6 mg | 10 | ig | 91.72 ± 12.34 | 58.43 ± 5.73 |
| scholaricine | 7 mg | 10 | ig | 93.61 ± 12.37 | 58.43 ± 7.04 |
| 19-epi-scholaricine | 2 mg | 10 | ig | 101.04 ± 9.25** | 61.32 ± 9.35 |

As compared to Sham group, $^\Delta P < 0.05$; as compared to Model group, */**P < 0.05/0.01

The experimental result showed: both the pharmaceutical composition and alkaloid composition of the invention could significantly enhance the activity of SOD in serum and lung homogenate (p<0.05/0.01); in addition, 19-epi-scholaricine could also significantly enhance the activity of SOD in serum (p<0.01); therefore, the pharmaceutical composition and alkaloid composition of the invention, and 19-epi-scholaricine could enhance the production of SOD, and reduce the aggravation of COPD caused by oxidative damage.

(5) Effect on malonaldehyde (MDA) in serum and lung homogenate of lipopolysaccharide plus smoke exposure-induced COPD model mouse:

Group and dose: in Test group 1, the ratio of picrinine, vallesamine, scholaricine and 19-epischolaricine by weight was 9:6:5:1, and the other groups and doses thereof were as described in Example 10.

Test index: MDA in serum and homogenate was used as index, and was determined by thibabituric acid method. The result was shown in Table 14.

TABLE 14

Effect on MDA in serum and homogenate of COPD model mouse
($\bar{x} \pm$ SD, nmol/mL)

| Group | dose (/kg) | Animal (number) | Administration route | Serum | Homogenate |
|---|---|---|---|---|---|
| Sham | — | 9 | ig | 9.78 ± 2.95 | 6.37 ± 0.61 |
| Model | 10 mL | 10 | ig | 13.73 ± 2.14▲ | 7.41 ± 0.54▲▲ |
| dexamethasone | 1 mg | 10 | ig | 14.04 ± 3.64 | 6.23 ± 0.60** |
| Test group 1 | 50 mg) | 10 | ig | 11.88 ± 2.29 | 6.63 ± 1.37 |
| Test group 2 | 25 mg | 10 | ig | 12.08 ± 6.40 | 6.23 ± 1.06 |
| Test group 3 | 10 mg | 10 | ig | 10.96 ± 2.64* | 6.21 ± 1.18* |
| picrinine | 10 mg | 10 | ig | 11.21 ± 4.46 | 6.17 ± 1.46 |
| vallesamine | 6 mg | 10 | ig | 11.07 ± 1.29** | 7.12 ± 1.44 |
| scholaricine | 7 mg | 10 | ig | 12.21 ± 3.38 | 6.09 ± 1.25* |
| 19-epi-scholaricine | 2 mg | 10 | ig | 10.94 ± 1.67* | 6.03 ± 0.66** |

As compared to Sham group, ▲▲p < 0.05/0.01;
as compared to Model group, */**P < 0.05/0.01

The experimental result showed: both the pharmaceutical composition and alkaloid composition of the invention could significantly decrease the content of MDA in serum and homogenate; in addition, vallesamine, scholaricine and 19-epi-scholaricine could also significantly decrease the content of MDA; therefore, the pharmaceutical composition, alkaloid composition, vallesamine, scholaricine and 19-epi-scholaricine of the invention could reduce the production of MDA, and reduce the aggravation of COPD caused by oxidative damage.

Example 11 Therapeutic Effect of the Pharmaceutical Composition and Alkaloid Composition of the Invention on Asthma Animal source: 25~30 g male ICR mouse, from laboratory animal department of Kunming Medical University, License No. SCXK (Dian) 2011-0004.

Method and route: ovalbumin (OVA) was used to induce mouse asthma model, and after intragastrical administration for 7 d at a dose of 20 mL/kg, the animal was sacrificed at the eighth day.

Group and dose: Control group, Model group, Positive control group, dexamethasone group (2 mg/kg), Test group 1: picrinine, vallesamine, scholaricine and 19-epischolaricine prepared in Example 1.7 were homogeneously mixed at different ratios by weight (50 mg/kg), Test group 2: the alkaloid composition prepared in Example 1.4 (25 mg/kg). Picrinine group (5 mg/kg), Vallesamine group (3.0 mg/kg), Scholaricine group (3.0 mg/kg), and 19-epischolaricine group (1.0 mg/kg).

Positive control drug: dexamethasone acetate tablet, Approval number: H33020822, 0.75 mg/tablet, produced by Zhejiang Xianju Pharmaceutical Co., Ltd., Batch No. 140329.

Sample preparation: all the samples were prepared by using 0.5% carboxymethylcellulose sodium (0.5% CMC-Na).

(1) Effect on Inflammatory Cell and Classification Thereof in Asthma Model Mouse:

Group and dose: in Test group 1, the ratio of picrinine, vallesamine, scholaricine and 19-epischolaricine by weight was 41:45:28:7, and the other groups and doses thereof were as described in Example 11.

Test index: number of white blood cells (WBCs) and number of eosinophil in bronchoalveolar lavage fluid (BALF) were used as index, and were determined by full-automatic hemocytometer. The result was shown in Table 15.

TABLE 15

Effect on WBC count and eosinophil percentage in BALF of asthma model mouse ($\bar{x} \pm$ SD)

| Group | dose (/kg) | Animal (number) | Number of WBCs (×10$^9$/L) | Eosinophil percentage (%) |
|---|---|---|---|---|
| Normal | — | 10 | 0.45 ± 0.19 | 0.02 ± 0.07 |
| Model | — | 10 | 1.17 ± 0.57▲▲ | 9.51 ± 4.61▲▲ |
| dexamethasone | 2 mg | 10 | 0.50 ± 0.17** | 4.32 ± 1.12** |
| Test group 1 | 50 mg | 11 | 0.58 ± 0.27* | 5.50 ± 1.61* |
| Test group 2 | 25 mg | 11 | 0.54 ± 0.17** | 5.34 ± 1.66* |
| picrinine | 5.0 mg | 11 | 0.91 ± 0.50 | 6.18 ± 3.61 |
| vallesamine | 3.0 mg | 11 | 0.73 ± 0.35 | 6.48 ± 2.84 |
| scholaricine | 3.0 mg | 11 | 0.60 ± 0.28* | 5.33 ± 1.62* |
| 19-epi-scholaricine | 3.5 mg | 11 | 0.75 ± 0.22 | 5.70 ± 2.63* |

As compared to Model group: */**p < 0.05/0.01,
as compared to Normal group: ▲▲p < 0.01

The experimental result showed: the pharmaceutical composition, alkaloid composition and the monomeric compounds scholaricine and 19-epi-scholaricine of the invention could significantly lower the total number of WBCs and the eosinophil percentage in BALF of model rat, and had a statistic difference as compared to Control group (P<0.05/0.01); thereby indicating that the pharmaceutical composition, alkaloid composition and the monomeric compounds scholaricine and 19-epi-scholaricine could effectively prevent aggregation of inflammatory cell in asthma model.

(2) Effect on Eosinophil Chemotactic Factor (Eotaxin) in Serum of Asthma Model Mouse:

Group and dose: in Test group 1, the ratio of picrinine, vallesamine, scholaricine and 19-epischolaricine by weight was 37:42:30:8, and the other groups and doses thereof were as described in Example 11.

Test index: eosinophil chemotactic factor (Eotaxin) in serum was used as index, and was determined by enzyme linked immunosorbent assay. The result was shown in Table 16.

TABLE 16

Effect on Eotaxin in serum of asthma model mouse
($\bar{x} \pm$ SD, pg/mL)

| Group | dose (/kg) | Administration route | Animal (number) | Eotaxin |
|---|---|---|---|---|
| Control | — | ig | 10 | 4.87 ± 0.60 |
| Model | — | ig | 10 | 10.58 ± 2.51▲▲ |

TABLE 16-continued

Effect on Eotaxin in serum of asthma model mouse
(x̄ ± SD, pg/mL)

| Group | dose (/kg) | Administration route | Animal (number) | Eotaxin |
|---|---|---|---|---|
| dexamethasone | 2.0 mg | ig | 10 | 7.87 ± 0.45** |
| Test group 1 | 50 mg | ig | 11 | 8.35 ± 0.61* |
| Test group 2 | 25 mg | ig | 11 | 8.47 ± 0.91* |
| picrinine | 5.0 mg | ig | 11 | 9.03 ± 1.80 |
| vallesamine | 3.0 mg | ig | 11 | 8.90 ± 2.36 |
| scholaricine | 3.0 mg | ig | 11 | 8.48 ± 0.63* |
| 19-epi-scholaricine | 3.5 mg | ig | 11 | 8.74 ± 1.40 |

As compared to Model group: */**p < 0.05/0.01,
as compared to Control group: ▲▲p < 0.01

The experimental result showed: the pharmaceutical composition, alkaloid composition and scholaricine of the invention could significantly reduce eosinophil chemotactic factor (Eotaxin) in serum of model mouse, and had a statistic difference as compared to Model group (P<0.05); thereby indicating that the pharmaceutical composition, alkaloid composition and scholaricine could effectively reduce the production of eosinophil chemotactic factor (Eotaxin) in serum of asthma model.

(3) Effect on Immunoglobulin IgE in Serum of Asthma Model Mouse:

Group and dose: In Test group 1, the ratio of picrinine, vallesamine, scholaricine and 19-epischolaricine by weight was 30:33:27:6, and the other groups and doses thereof were as described in Example 11.

Test index: immunoglobulin IgE in serum was used as index, and was determined by enzyme linked immunosorbent assay. The result was shown in Table 17.

TABLE 17

Effect on IgE in serum of asthma model mouse (x̄ ± SD, μg/mL)

| Group | dose (/kg) | Administration route | Animal (number) | IgE |
|---|---|---|---|---|
| Control | — | ig | 10 | 2.56 ± 0.50 |
| Model | — | ig | 10 | 4.58 ± 1.32▲▲ |
| dexamethasone | 2.0 mg | ig | 10 | 3.23 ± 0.53 g |
| Test group 1 | 50 mg | ig | 11 | 3.34 ± 0.93* |
| Test group 2 | 25 mg | ig | 11 | 3.38 ± 0.80* |
| picrinine | 5.0 mg | ig | 11 | 3.85 ± 0.72 |
| vallesamine | 3.0 mg | ig | 11 | 3.57 ± 0.99 |
| scholaricine | 3.0 mg | ig | 11 | 3.39 ± 0.80* |
| 19-epi-scholaricine | 3.5 mg | ig | 11 | 3.55 ± 0.87 | as compared to Model group: *p < 0.05/0.01,
as compared to Control group: ▲▲p < 0.01

The experimental result showed: the pharmaceutical composition, alkaloid composition and scholaricine of the invention could significantly suppress the production of immunoglobulin IgE in serum of asthma model mouse, and had a statistic difference as compared to Model group (P<0.05); thereby indicating that the pharmaceutical composition, alkaloid composition and scholaricine could effectively reduce the production of IgE in serum of asthma model, and significantly alleviate symptom of asthma.

(4) Effect on Interleukin-4 (IL-4) in Bronchoalveolar Lavage Fluid (BALF) of Asthma Model Mouse:

Group and dose: in Test group 1, the ratio of picrinine, vallesamine, scholaricine and 19-epischolaricine by weight was 25:18:15:3, and the other groups and doses thereof were as described in Example 11.

Test index: immunoglobulin IL-4 in serum was used as index, and was determined by enzyme linked immunosorbent assay. The result was shown in Table 18.

TABLE 18

Effect on IL-4 in BALF of asthma model mouse (x̄ ± SD, pg/mL)

| Group | dose (/kg) | Administration route | Animal (number) | IL-4 |
|---|---|---|---|---|
| Control | — | ig | 10 | 7.45 ± 2.91 |
| Model | — | ig | 10 | 16.69 ± 6.57▲▲ |
| dexamethasone | 2.0 mg | ig | 10 | 9.96 ± 4.03* |
| Test group 1 | 50 mg | ig | 11 | 10.43 ± 1.88* |
| Test group 2 | 25 mg | ig | 11 | 10.97 ± 3.08* |
| picrinine | 5.0 mg | ig | 11 | 12.60 ± 4.39 |
| vallesamine | 3.0 mg | ig | 11 | 11.61 ± 2.40* |
| scholaricine | 3.0 mg | ig | 11 | 11.21 ± 3.62* |
| 19-epi-scholaricine | 3.5 mg | ig | 11 | 11.16 ± 3.58* |

As compared to Model group: *p < 0.05,
as compared to Normal group: ▲▲p < 0.01

The experimental result showed: the pharmaceutical composition, alkaloid composition and four monomeric compounds of the invention could significantly suppress the production of IL-4 in BALF of asthma model mouse, and had a statistic difference as compared to Model group (P<0.05); thereby indicating that the pharmaceutical composition, alkaloid composition and four monomeric compounds could effectively reduce the production of IL-4 in BALF of asthma model, and significantly alleviate symptom of asthma.

(5) Effect on Interleukin-10 (IL-10) in Bronchoalveolar Lavage Fluid (BALF) of Asthma Model Mouse:

Group and dose: in Test group 1, the ratio of picrinine, vallesamine, scholaricine and 19-epischolaricine by weight was 18:13:14:3, and the other groups and doses thereof were as described in Example 11.

Test index: IL-10 in BALF was used as index, and was determined by enzyme linked immunosorbent assay. The result was shown in Table 19.

TABLE 19

Effect on IL-10 in BALF of asthma model mouse
(x̄ ± SD, pg/mL)

| Group | dose (/kg) | Administration route | Animal (number) | IL-10 |
|---|---|---|---|---|
| Control | — | ig | 10 | 24.99 ± 5.58 |
| Model | — | ig | 10 | 11.60 ± 3.11▲▲ |
| dexamethasone | 2.0 mg | ig | 10 | 17.45 ± 5.60* |
| Test group 1 | 50 mg | ig | 11 | 16.06 ± 3.21** |
| Test group 2 | 25 mg | ig | 11 | 16.03 ± 3.70* |
| picrinine | 5.0 mg | ig | 11 | 13.00 ± 3.15 |
| vallesamine | 3.0 mg | ig | 11 | 14.83 ± 3.49 |
| scholaricine | 3.0 mg | ig | 11 | 16.83 ± 3.87** |
| 19-epi-scholaricine | 3.5 mg | ig | 11 | 16.56 ± 4.92* |

As compared to Model group: */**p < 0.05/0.01,
as compared to Control group: ▲▲ < 0.01

The experimental result showed: the pharmaceutical composition, alkaloid composition, scholaricine, and 19-epi-scholaricine of the invention could significantly enhance the production of IL-10 in BALF of asthma model mouse, and had a statistic difference as compared to Model group (P<0.05/0.01); thereby indicating that the pharmaceutical composition, alkaloid composition, scholaricine, and 19-epi-scholaricine could effectively promote the production of IL-10 in BALF of asthma model, and significantly alleviate symptom of asthma.

(6) Effect on Superoxide Dismutase (SOD) in Serum and Bronchoalveolar Lavage Fluid (BALF) of Asthma Model Mouse:

Group and dose: in Test group 1, the ratio of picrinine, vallesamine, scholaricine and 19-epischolaricine by weight was 12:10:9:2, and the other groups and doses thereof were as described in Example 11.

Test index: SOD in serum and BALF was used as index, and was determined by xanthine oxidase method. The result was shown in Table 20.

TABLE 20

Effect on SOD in serum and BALF of asthma model mouse
($\bar{x}$ ± SD, U/mL)

| Group | Administration dose (/kg) | route | Animal (number) | SOD serum | lavage fluid |
|---|---|---|---|---|---|
| Control | — | ig | 10 | 86.09 ± 6.66 | 81.42 ± 8.02 |
| Model | — | ig | 10 | 64.79 ± 8.59▲▲ | 59.57 ± 11.83▲▲ |
| dexamethasone | 2.0 mg | ig | 10 | 74.83 ± 8.43* | 76.57 ± 12.52** |
| Test group 1 | 50 mg | ig | 11 | 75.58 ± 9.60* | 74.80 ± 7.59** |
| Test group 2 | 25 mg | ig | 11 | 74.09 ± 6.26* | 70.64 ± 5.89* |
| picrinine | 5.0 mg | ig | 11 | 70.31 ± 7.30 | 62.32 ± 8.22 |
| vallesamine | 3.0 mg | ig | 11 | 70.53 ± 7.77 | 70.88 ± 8.52* |
| scholaricine | 3.0 mg | ig | 11 | 73.36 ± 8.44* | 76.78 ± 8.01** |
| 19-epi-scholaricine | 3.5 mg | ig | 11 | 73.85 ± 7.93* | 71.82 ± 12.39* |

As compared to Model group: */**$p < 0.05/0.01$,
as compared to Control group: ▲▲$p < 0.01$ The experimental result showed: the pharmaceutical composition, alkaloid composition and four monomeric compounds of the invention could significantly promote the production of SOD in BALF of asthma model mouse, and had a statistic difference as compared to Model group ($P<0.05/0.01$); thereby indicating that the pharmaceutical composition, alkaloid composition and four monomeric compounds could effectively enhance the activity of SOD in serum and BALF of asthma model, and enhance the antioxidant effect.

(7) Effect on Lipid Peroxidation Product (MDA) in Serum and Bronchoalveolar Lavage Fluid (BALF) of Asthma Model Mouse:

Group and dose: in Test group 1, the ratio of picrinine, vallesamine, scholaricine and 19-epischolaricine by weight was 8:6:5:1, and the other groups and doses thereof were as described in Example 11.

Test index: MDA in serum and BALF was used as index, and was determined by thiobarbituric acid method. The result was shown in Table 21.

production of MDA in BALF of asthma model mouse, and had a statistic difference as compared to Model group ($P<0.05/0.01$); thereby indicating that the pharmaceutical composition, alkaloid composition and four monomeric compounds could effectively reduce the production of lipid peroxidation product in serum and BALF of asthma model, and reduce peroxidative damage.

Example 12 Therapeutic Effect of the Pharmaceutical Composition and Alkaloid Composition of the Invention on Pulmonary Fibrosis Animal source: 30~35 g male ICR mouse, from laboratory animal department of Kunming Medical University, License No. SCXK (Dian) 2011-0004.

Method and route: bleomycin was used to induce mouse pulmonary fibrosis, and after intragastrical administration for 28 d at a dose of 20 mL/kg, the animal was sacrificed at the 29th day.

Group and dose: Sham group, Model group, Positive control group, prednisone acetate (5 mg/kg) group, Test group 1: picrinine, vallesamine, scholaricine and 19-epischolaricine prepared in Example 1.7 were mixed at different ratios by weight (50 mg/kg), Test group 2: the alkaloid

TABLE 21

Effect on MDA in serum and BALF of asthma model mouse
($\bar{x}$ ± SD, nmol/mL)

| Group | Administration dose (/kg) | route | Animal (number) | MDA serum | lavage fluid |
|---|---|---|---|---|---|
| Control | — | ig | 10 | 8.77 ± 2.06 | 1.90 ± 0.38 |
| Model | — | ig | 10 | 16.92 ± 1.41▲▲ | 4.25 ± 1.851▲▲ |
| dexamethasone | 2.0 mg | ig | 10 | 10.99 ± 2.38** | 2.17 ± .17** |
| Test group 1 | 50 mg | ig | 11 | 9.47 ± 1.98** | 2.56 ± .56** |
| Test group 2 | 25 mg | ig | 11 | 9.07 ± 1.96** | 2.55 ± 1.19* |
| picrinine | 5.0 mg | ig | 11 | 14.03 ± 5.71 | 3.29 ± 2.07 |
| vallesamine | 3.0 mg | ig | 11 | 13.36 ± 6.10 | 2.92 ± 1.48 |
| scholaricine | 3.0 mg | ig | 11 | 9.19 ± 2.77** | 2.43 ± 1.05* |
| 19-epi-scholaricine | 3.5 mg | ig | 11 | 13.55 ± 4.66 | 2.55 ± 1.47* |

As compared to Model group: */**$p < 0.05/0.01$,
as compared to Control group: ▲▲$p < 0.01$ The experimental result showed: the pharmaceutical composition, alkaloid composition, and the four monomeric compounds of the invention could significantly reduce the composition (25 mg/kg) prepared in Example 1.5, Test group 3: the alkaloid composition (12.5 mg/kg) prepared in Example 1.6, Picrinine group (5.0 mg/kg), Vallesamine group (3.0 mg/kg), Scholaricine group (3.5 mg/kg), and 19-epischolaricine group (1.0 mg/kg).

Positive control drug: prednisone acetate tablet, Approval number: H33021207, 5 mg/tablet, produced by Zhejiang Xianju Pharmaceutical Co., Ltd., Batch No. 140146.

Sample preparation: all the samples were prepared by using 0.5% carboxymethylcellulose sodium (0.5% CMC-Na).

(1) Effect on Krebs Von Den Lungen-6 (KL-6) in Serum of Pulmonary Fibrosis Model Mouse:

Group and dose: in Test group 1, the ratio of picrinine, vallesamine, scholaricine and 19-epischolaricine by weight was 45:38:30:8, and the other groups and doses thereof were as described in Example 12.

Test index: KL-6 in serum was used as index, and was determined by enzyme linked immunosorbent assay. The result was shown in Table 22.

TABLE 22

Effect on KL-6 in serum of pulmonary fibrosis model mouse ($\bar{x} \pm SD$, U/mg prot)

| Group | dose (/kg) | Administration route | Animal (number) | KL-6 |
|---|---|---|---|---|
| Sham | — | Ig | 10 | 2.52 ± 1.44 |
| Model | — | Ig | 10 | 5.12 ± 1.94▲▲ |
| prednisone acetate | 5 mg | Ig | 10 | 3.00 ± 1.00** |
| Test group 1 | 50 mg | Ig | 10 | 3.32 ± 1.24* |
| Test group 2 | 25 mg | Ig | 10 | 3.39 ± 1.40* |
| Test group 3 | 12.5 mg | Ig | 10 | 3.56 ± 2.02 |
| picrinine | 5.0 mg | Ig | 10 | 3.91 ± 0.60 |
| vallesamine | 3.0 mg | Ig | 10 | 3.62 ± 0.87* |
| scholaricine | 3.5 mg | Ig | 10 | 3.72 ± 0.79* |
| 19-epi-scholaricine | 1.0 mg | Ig | 10 | 4.10 ± 0.97 |

As compared to Model group: */**p < 0.05/0.01,
as compared to Sham group: ▲▲p < 0.01

The experimental result showed: the pharmaceutical composition alkaloid composition, vallesamine and scholaricine of the invention could significantly reduce the production of KL-6 in serum of pulmonary fibrosis model mouse, and had a statistic difference as compared to Model group (P<0.05); thereby indicating that the pharmaceutical composition, alkaloid composition, vallesamine and scholaricine could effectively reduce the production of KL-6 in serum of pulmonary fibrosis model, and alleviate the injury to alveolar epithelial cell.

(2) Effect on Lactate Dehydrogenase (LDH) in Serum of Pulmonary Fibrosis Model Mouse:

Group and dose: In Test group 1, the ratio of picrinine, vallesamine, scholaricine and 19-epischolaricine by weight was 35:28:23:6, and the other groups and doses thereof were as described in Example 12.

Test index: LDH in serum was used as index, and was determined by 2, 4-dinitrophenylhydrazine method. The result was shown in Table 23.

TABLE 23

Effect on LDH in serum of pulmonary fibrosis model mouse ($\bar{x} \pm SD$, U/g prot)

| Group | dose (/kg) | Administration route | Animal (number) | LDH |
|---|---|---|---|---|
| Sham | — | ig | 10 | 9.8 ± 3.2 |
| Model | — | ig | 10 | 15.6 ± 5.1▲▲ |

TABLE 23-continued

Effect on LDH in serum of pulmonary fibrosis model mouse ($\bar{x} \pm SD$, U/g prot)

| Group | dose (/kg) | Administration route | Animal (number) | LDH |
|---|---|---|---|---|
| prednisone acetate | 5 mg | ig | 10 | 10.5 ± 3.4* |
| Test group 1 | 50 mg | ig | 10 | 10.7 ± 2.2* |
| Test group 2 | 25 mg | ig | 10 | 11.2 ± 2.8* |
| Test group 3 | 12.5 mg | ig | 10 | 10.8 ± 2.8* |
| picrinine | 5.0 mg | ig | 10 | 11.9 ± 2.3* |
| vallesamine | 3.0 mg | ig | 10 | 10.6 ± 2.2* |
| scholaricine | 3.5 mg | ig | 10 | 12.5 ± 3.2 |
| 19-epi-scholaricine | 1.0 mg | ig | 10 | 11.9 ± 2.2* | as compared to Model group: *p < 0.05,
As compared to Sham group: ▲▲p < 0.01

The experimental result showed: the pharmaceutical composition, alkaloid composition, picrinine, vallesamine and 19-epi-scholaricine of the invention could significantly reduce the production of LDH in serum of pulmonary fibrosis model mouse, and had a statistic difference as compared to Model group (P<0.05); thereby indicating that the pharmaceutical composition, alkaloid composition, picrinine, vallesamine and 19-epi-scholaricine could effectively reduce the production of LDH in serum of pulmonary fibrosis model, and alleviate the injury to alveolar epithelial cell.

(3) Effect on Transforming Growth Factor (TGF-β) in Homogenate of Pulmonary Fibrosis Model Mouse:

Group and dose: in Test group 1, the ratio of picrinine, vallesamine, scholaricine and 19-epischolaricine by weight was 25:18:16:4, and the other groups and doses thereof were as described in Example 12.

Test index: TGF-β in homogenate was used as index, and was determined by enzyme linked immunosorbent assay. The result was shown in Table 24.

TABLE 24

Effect on TGF-β in homogenate of pulmonary fibrosis model mouse ($\bar{x} \pm SD$, mg/g prot)

| Group | dose (/kg) | Administration route | Animal (number) | TGF-β |
|---|---|---|---|---|
| Sham | — | ig | 10 | 39.4 ± 12.5 |
| Model | — | ig | 10 | 67.2 ± 24.1▲▲ |
| prednisone acetate | 5 mg | ig | 10 | 45.2 ± 14.0* |
| Test group 1 | 50 mg | ig | 10 | 46.2 ± 21.0 |
| Test group 2 | 25 mg | ig | 10 | 47.9 ± 15.1* |
| Test group 3 | 12.5 mg | ig | 10 | 41.5 ± 19.3* |
| picrinine | 5.0 mg | ig | 10 | 40.7 ± 12.5** |
| vallesamine | 3.0 mg | ig | 10 | 56.5 ± 17.6 |
| scholaricine | 3.5 mg | ig | 10 | 46.5 ± 12.3* |
| 19-epi-scholaricine | 1.0 mg | ig | 10 | 60.2 ± 17.7 |

As compared to Model group: *p < 0.05,
as compared to Sham group: ▲▲p < 0.01

The experimental result showed: the pharmaceutical composition, alkaloid composition, picrinine and scholaricine of the invention could significantly reduce the production of TGF-β in homogenate of pulmonary fibrosis model mouse, and had a statistic difference as compared to Model group (P<0.05/0.01); thereby indicating that the pharmaceutical composition, alkaloid composition, picrinine and scholaricine could effectively reduce the production of TGF-β in homogenate of pulmonary fibrosis model, and reduce fibrosis.

(4) Effect on Collagen I (Col-1) in Homogenate of Pulmonary Fibrosis Model Mouse:

Group and dose: in Test group 1, the ratio of picrinine, vallesamine, scholaricine and 19-epischolaricine by weight was 20:17:17:4, and the other groups and doses thereof were as described in Example 12.

Test index: Col-1 in homogenate was used as index, and was determined by enzyme linked immunosorbent assay. The result was shown in Table 25.

TABLE 25

Effect on Col-1 in homogenate of pulmonary fibrosis model mouse ($\bar{x} \pm SD$, μg/g prot)

| Group | dose (/kg) | Administration route | Animal (number) | Col-1 |
|---|---|---|---|---|
| Sham | — | ig | 10 | 4.4 ± 1.2 |
| Model | — | ig | 10 | 8.2 ± 1.4▲▲ |
| prednisone acetate | 5 mg | ig | 10 | 6.0 ± 2.1* |
| Test group 1 | 50 mg | ig | 10 | 5.6 ± 1.9** |
| Test group 2 | 25 mg | ig | 10 | 6.4 ± 2.0* |
| Test group 3 | 12.5 mg | ig | 10 | 5.1 ± 2.6** |
| picrinine | 5.0 mg | ig | 10 | 4.5 ± 2.3** |
| vallesamine | 3.0 mg | ig | 10 | 6.3 ± 2.7 |
| scholaricine | 3.5 mg | ig | 10 | 5.9 ± 2.1** |
| 19-epi-scholaricine | 1.0 mg | ig | 10 | 6.5 ± 2.2 |

As compared to Model group: */**$p < 0.05/0.01$,
as compared to Sham group: ▲▲$p < 0.01$ The experimental result showed: the pharmaceutical composition, alkaloid composition, picrinine and scholaricine of the invention could significantly reduce the production of Col-1 in homogenate of pulmonary fibrosis model mouse, and had a statistic difference as compared to Model group ($P<0.05/0.01$); thereby indicating that the pharmaceutical composition, alkaloid composition, picrinine and scholaricine could effectively reduce the production of Col-1 in homogenate of pulmonary fibrosis model, and reduce collagenic fibrosis.

(5) Effect on Hydroxyproline (Hyp) in Homogenate of Pulmonary Fibrosis Model Mouse:

Group and dose: in Test group 1, the ratio of picrinine, vallesamine, scholaricine and 19-epischolaricine by weight was 15:11:12:3, and the other groups and doses thereof were as described in Example 12.

Test index: Hyp in homogenate was used as index, and was determined by enzyme linked immunosorbent assay. The result was shown in Table 26.

TABLE 26

Effect on Hyp in homogenate of pulmonary fibrosis model mouse ($\bar{x} \pm SD$, μg/g prot)

| Group | dose (/kg) | Administration route | Animal (number) | Hyp |
|---|---|---|---|---|
| Sham | — | ig | 10 | 4.4 ± 1.2 |
| Model | — | ig | 10 | 8.5 ± 2.7▲▲ |
| prednisone acetate | 5 mg | ig | 10 | 2.9 ± 0.8 |
| Test group 1 | 50 mg | ig | 10 | 7.7 ± 1.7 |
| Test group 2 | 25 mg | ig | 10 | 6.1 ± 2.4* |
| Test group 3 | 12.5 mg | ig | 10 | 3.1 ± 1.3** |
| picrinine | 5.0 mg | ig | 10 | 5.6 ± 1.4** |
| vallesamine | 3.0 mg | ig | 10 | 5.5 ± 1.7** |
| scholaricine | 3.5 mg | ig | 10 | 6.5 ± 1.5 |
| 19-epi-scholaricine | 1.0 mg | ig | 10 | 6.0 ± 2.2* |

As compared to Model group: *$p < 0.05$,
as compared to Sham group: ▲▲$p < 0.01$ The experimental result showed: the pharmaceutical composition, alkaloid composition, picrinine, vallesamine and 19-epi-scholaricine of the invention could significantly reduce the production of Hyp in homogenate of pulmonary fibrosis model mouse, and had a statistic difference as compared to Model group ($P<0.05/0.01$); thereby indicating that the pharmaceutical composition, alkaloid composition, picrinine, vallesamine and 19-epi-scholaricine could effectively reduce the production of Hyp in homogenate of pulmonary fibrosis model.

(6) Effect on Superoxide Dismutase (SOD) in Serum and Homogenate of Pulmonary Fibrosis Model Mouse:

Group and dose: in Test group 1, the ratio of picrinine, vallesamine, scholaricine and 19-epischolaricine by weight was 10:7:7:2, and the other groups and doses thereof were as described in Example 12.

Test index: SOD in serum and homogenate was used as index, and was determined by xanthine oxidase method. The result was shown in Table 27.

TABLE 27

Effect on SOD in serum and homogenate of pulmonary fibrosis model mouse ($\bar{x} \pm SD$, U/mg prot)

| Group | Dose (/kg) | Administration route | Animal (number) | Serum | Homogenate |
|---|---|---|---|---|---|
| Sham | — | ig | 10 | 19.1 ± 7.8 | 79.6 ± 9.7 |
| Model | — | ig | 10 | 12.4 ± 2.1▲ | 44.7 ± 9.7▲▲ |
| prednisone acetate | 5 mg | ig | 10 | 15.5 ± 3.8* | 60.0 ± 15.9* |
| Test group 1 | 50 mg | ig | 10 | 14.5 ± 5.4 | 52.2 ± 8.7 |
| Test group 2 | 25 mg | ig | 10 | 15.8 ± 5.8 | 61.4 ± 8.5** |
| Test group 3 | 12.5 mg | ig | 10 | 17.8 ± 6.7* | 55.5 ± 11.1* |
| picrinine | 5.0 mg | ig | 10 | 17.2 ± 5.1 | 53.2 ± 8.9 |
| vallesamine | 3.0 mg | ig | 10 | 14.2 ± 3.4 | 54.9 ± 10.7* |
| scholaricine | 3.5 mg | ig | 10 | 16.1 ± 4.9 | 63.0 ± 16.8** |
| 19-epi-scholaricine | 1.0 mg | ig | 10 | 15.0 ± 4.4 | 66.0 ± 9.8** |

As compared to Model group: */**$p < 0.05/0.01$,
as compared to Sham group: ▲▲$p < 0.01$ The experimental result showed: the pharmaceutical composition, alkaloid composition, vallesamine, scholaricine and 19-epi-scholaricine of the invention could significantly enhance the activity of SOD in serum and homogenate of pulmonary fibrosis model mouse, and had a statistic difference as compared to Model group ($P<0.05/0.01$); thereby indicating that the pharmaceutical composition, alkaloid composition, vallesamine, scholaricine and 19-epi-scholaricine could effectively enhance the antioxidant activity in serum and homogenate of pulmonary fibrosis model, and reduce fibrosis.

(7) Effect on Lipid Peroxidation Product (MDA) in Serum and Homogenate of Pulmonary Fibrosis Model Mouse:

Group and dose: in Test group 1, the ratio of picrinine, vallesamine, scholaricine and 19-epischolaricine by weight was 8:5:5:1, and the other groups and doses thereof were as described in Example 12.

Test index: MDA in serum and homogenate was used as index, and was determined by thiobabituric acid method. The result was shown in Table 28.

TABLE 28

Effect on MDA in serum and homogenate of pulmonary fibrosis model mouse ($\bar{x} \pm SD$, nmol/mg prot)

| Group | Dose (/kg) | Administration route | Animal (number) | Serum | Homogenate |
|---|---|---|---|---|---|
| Sham | — | ig | 10 | 0.49 ± 0.22 | 17.7 ± 7.5 |
| Model | — | ig | 10 | 0.91 ± 0.39▲▲ | 25.7 ± 3.8▲▲ |
| prednisone acetate | 5 mg | ig | 10 | 0.55 ± 0.17* | 19.0 ± 6.6* |
| Test group 1 | 50 mg | ig | 10 | 0.57 ± 0.13* | 17.4 ± 9.7* |
| Test group 2 | 25 mg | ig | 10 | 0.60 ± 0.15* | 20.1 ± 6.9* |
| Test group 3 | 12.5 mg | ig | 10 | 0.55 ± 0.18* | 21.2 ± 2.7** |
| picrinine | 5.0 mg | ig | 10 | 0.62 ± 0.18* | 21.7 ± 4.2* |
| vallesamine | 3.0 mg | ig | 10 | 0.66 ± 0.24 | 19.9 ± 7.7* |
| scholaricine | 3.5 mg | ig | 10 | 0.64 ± 0.17 | 21.9 ± 4.3* |
| 19-epi-scholaricine | 1.0 mg | ig | 10 | 0.66 ± 0.18 | 22.0 ± 7.4 | as compared to Model group: */**$p < 0.05/0.01$,
As compared to Sham group: ▲▲$p < 0.01$ The experimental result showed: the pharmaceutical composition, alkaloid composition, picrinine, vallesamine and scholaricine of the invention could significantly reduce the production of MDA in serum and homogenate of pulmonary fibrosis model mouse, and had a statistic difference as compared to Model group ($P<0.05/0.01$); thereby indicating that the pharmaceutical composition, alkaloid composition, picrinine, vallesamine and scholaricine could reduce the production of peroxides in serum and homogenate of pulmonary fibrosis model, and reduce the fibrosis.

Although the embodiments of the invention have been described in detail, a person skilled in the art would understand that a variety of modifications and replacements may be performed to the details according to all the teachings disclosed therein. These changes all fall into the protection scope of the invention. The scope of the invention is defined by the attached claims and any equivalent thereof.

The invention claimed is:

1. A method for treating chronic obstructive pulmonary disease or pulmonary fibrosis disease, comprising administering to a subject in need thereof a therapeutically effective amount of
   a) a pharmaceutical composition, comprising one or more components selected from picrinine, vallesamine, scholaricine and 19-epischolaricine;
   b) an alkaloid composition extracted from leaves of Alstonia scholaris, comprising 8-50 parts by weight of picrinine, 5-45 parts by weight of vallesamine, 5-30 parts by weight of scholaricine and 0-10 parts by weight of 19-epischolaricine;
   c) an alkaloid composition extracted from leaves of Alstonia scholaris, which is prepared by Method 1 or Method 2:

Method 1:
   i) leaves of Alstonia scholaris are extracted with ethanol or an ethanol aqueous solution, and the extract is collected and concentrated to obtain a concrete;
   ii) the concrete is soaked with hydrochloric acid or sulfuric acid for 1-5 times, and filtered to collect a filtrate;
   iii) the filtrate is loaded to an ion exchange resin, and eluted with water and ethanol-ammonia water, respectively;
   iv) the eluent eluted by the ethanol-ammonia water is collected and concentrated, to obtain the alkaloid composition of leaves of Alstonia scholaris;

Method 2:
   (1) leaves of Alstonia scholaris are extracted with ethanol or an ethanol aqueous solution, and the extract is collected and concentrated to obtain a concrete;
   (2) the concrete is soaked with hydrochloric acid or sulfuric acid, and filtered;
   (3) the filtrate is collected and concentrated, to obtain an acidic ethanol extract;
   (4) the acidic ethanol extract is dissolved in water, adjusted to have a basic pH, and extracted with ethyl acetate; and
   (5) the ethyl acetate phase is collected and concentrated, to obtain the alkaloid composition of leaves of Alstonia scholaris or
   d) a composition comprising picrinine, vallesamine, scholaricine, 19-epischolaricine or any combination thereof.

2. The method according to claim 1, wherein the chronic obstructive pulmonary disease has any of the following causes: smoking, infection, a physical and chemical factor, and air pollution.

3. The method according to claim 2, wherein the pulmonary fibrosis disease has any of the following causes: smoking, asbestos, inorganic dust, a drug, radiation injury, a harmful gas, infection, an environmental factor, and pneumopathy.

4. The method according to claim 1, wherein the pharmaceutical composition comprises 8-50 parts by weight of picrinine, 5-45 parts by weight of vallesamine, 5-30 parts by weight of scholaricine, and 0-10 parts by weight of 19-epischolaricine.

5. The method according to claim 4, wherein picrinine in the pharmaceutical composition is in an amount of 8-16 parts by weight.

6. The method according to claim 4, wherein vallesamine in the pharmaceutical composition is in an amount of 5-15 parts by weight.

7. The method according to claim 4, wherein scholaricine in the pharmaceutical composition is in an amount of 5-10 parts by weight.

8. The method according to claim 4, wherein 19-epischolaricine in the pharmaceutical composition is in an amount of 1-5 parts by weight.

9. The method according to claim 1, wherein the pharmaceutical composition comprises 8-16 parts by weight of picrinine, 5-15 parts by weight of vallesamine, 5-10 parts by weight of scholaricine, and 1-5 parts by weight of 19-epischolaricine.

10. The method according to claim 1, wherein the pharmaceutical composition comprises 8-12 parts by weight of picrinine, 5-9 parts by weight of vallesamine, 5-9 parts by weight of scholaricine, and 1-3 parts by weight of 19-epischolaricine.

11. The method according to claim 1, wherein the pharmaceutical composition comprises about 10 parts by weight of picrinine, 7 parts by weight of vallesamine, 7 parts by weight of scholaricine, and 2 parts by weight of 19-epischolaricine.

12. The method according to claim 1, wherein the alkaloid composition of b) comprises 8-16 parts by weight of picrinine, 5-15 parts by weight of vallesamine, 5-10 parts by weight of scholaricine, and 1-5 parts by weight of 19-epischolaricine.

13. The method according to claim 1, wherein the alkaloid composition of b) comprises 8-12 parts by weight of picrinine, 5-9 parts by weight of vallesamine, 5-9 parts by weight of scholaricine and 1-3 parts by weight of 19-epischolaricine.

14. The method according to claim 1, wherein the alkaloid composition of b) comprises about 10 parts by weight of picrinine, 7 parts by weight of vallesamine, 7 parts by weight of scholaricine and 2 parts by weight of 19-epischolaricine.

15. The method according to claim 1, wherein Method 1 and Method 2 are characterized by one or more items selected from the group consisting of:
(1) in Method 1 or Method 2, each kilogram of leaves of *Alstonia scholaris* is extracted with 1-20 liters of ethanol or an ethanol aqueous solution;
(2) in Method 1 or Method 2, the ethanol aqueous solution has a mass fraction of 50-95%;
(3) in Method 1 or Method 2, leaves of *Alstonia scholaris* are extracted under heating;
(4) in Method 1 or Method 2, the hydrochloric acid has a mass fraction of 0.1-20%;
(5) in Method 1 or Method 2, the sulfuric acid has a mass fraction of 0.01-10%;
(6) in Method 1 or Method 2, the hydrochloric acid or sulfuric acid is used in such an amount that the filtrate has a pH of 2-6;
(7) in Method 1, the ion exchange resin is a cation exchange resin;
(8) in Method 1, ethanol and ammonia water is in a volume ratio of (1-10):1 in the ethanol-ammonia water;
(9) in step (2) of Method 2, each kilogram of the acidic ethanol extract is dissolved with water in an amount of 1-15 L;
(10) in step (2) of Method 2, the pH is adjusted by ammonia water, NaOH aqueous solution, KOH aqueous solution or $Na_2CO_3$ aqueous solution;
(11) in step (2) of Method 2, the basic pH is 7.5-11.

* * * * *

UNITED STATES PATENT AND TRADEMARK OFFICE
CERTIFICATE OF CORRECTION

PATENT NO. : 10,603,345 B2
APPLICATION NO. : 15/775372
DATED : March 31, 2020
INVENTOR(S) : X. Luo et al.

It is certified that error appears in the above-identified patent and that said Letters Patent is hereby corrected as shown below:

In the Claims

| Column | Line | |
|---|---|---|
| 46 | 61 | Please change "The method according to claim 2" to |
| (Claim 3, | 1) | "The method according to claim 1" |

Signed and Sealed this
Fifth Day of July, 2022

Katherine Kelly Vidal
*Director of the United States Patent and Trademark Office*